(12) United States Patent
Scully et al.

(10) Patent No.: US 8,942,780 B2
(45) Date of Patent: *Jan. 27, 2015

(54) DC MAGNETIC-BASED POSITION AND ORIENTATION MONITORING SYSTEM FOR TRACKING MEDICAL INSTRUMENTS

(75) Inventors: Jack T. Scully, Colchester, VT (US); Mark R. Schneider, Williston, VT (US)

(73) Assignee: Ascension Technology Corporation, Shelburne, VT (US)

( * ) Notice: Subject to any disclaimer, the term of this patent is extended or adjusted under 35 U.S.C. 154(b) by 392 days.

This patent is subject to a terminal disclaimer.

(21) Appl. No.: 12/924,476

(22) Filed: Sep. 29, 2010

(65) Prior Publication Data
US 2011/0082366 A1    Apr. 7, 2011

Related U.S. Application Data

(63) Continuation of application No. 11/242,048, filed on Oct. 4, 2005, now Pat. No. 7,835,785.

(51) Int. Cl.
*A61B 5/00*    (2006.01)
*A61B 5/06*    (2006.01)

(52) U.S. Cl.
CPC ........................ *A61B 5/06* (2013.01)
USPC ........... 600/407; 600/410; 600/424; 600/425; 600/437

(58) Field of Classification Search
USPC ........................ 600/407, 410, 424, 425, 437
See application file for complete search history.

(56) References Cited

U.S. PATENT DOCUMENTS

| 4,422,139 A | 12/1983 | Burkhead |
| 4,945,305 A * | 7/1990 | Blood .................... 324/207.17 |
| 5,453,686 A | 9/1995 | Anderson |
| 5,767,669 A | 6/1998 | Hansen et al. |
| 5,831,260 A | 11/1998 | Hansen |
| 6,379,302 B1 * | 4/2002 | Kessman et al. ............... 600/437 |
| 6,450,964 B1 | 9/2002 | Webler |
| 6,503,249 B1 | 1/2003 | Krause |
| 6,506,148 B2 * | 1/2003 | Loos ............................. 600/27 |
| 6,517,491 B1 | 2/2003 | Thiele et al. |
| 6,528,989 B1 | 3/2003 | Hansen |
| 6,535,756 B1 | 3/2003 | Simon et al. |
| 6,592,520 B1 | 7/2003 | Peszynski et al. |
| 6,724,191 B1 | 4/2004 | Larsen |

(Continued)

*Primary Examiner* — Peter Luong

(74) *Attorney, Agent, or Firm* — Fish & Richardson P.C.

(57) ABSTRACT

Miniaturized, five and six degrees-of-freedom magnetic sensors, responsive to pulsed DC magnetic fields waveforms generated by multiple transmitter options, provide an improved and cost-effective means of guiding medical instruments to targets inside the human body. The end result is achieved by integrating DC tracking, 3D reconstructions of pre-acquired patient scans and imaging software into a system enabling a physician to internally guide an instrument with real-time 3D vision for diagnostic and interventional purposes. The integration allows physicians to navigate within the human body by following 3D sensor tip locations superimposed on anatomical images reconstructed into 3D volumetric computer models. Sensor data can also be integrated with real-time imaging modalities, such as endoscopes, for intrabody navigation of instruments with instantaneous feedback through critical anatomy to locate and remove tissue. To meet stringent medical requirements, the system generates and senses pulsed DC magnetic fields embodied in an assemblage of miniaturized, disposable and reposable sensors functional with both dipole and co-planar transmitters.

20 Claims, 13 Drawing Sheets

3D Guidance System for Image-Guided Procedures

(56) References Cited

U.S. PATENT DOCUMENTS

| | | | |
|---|---|---|---|
| 6,748,098 B1 * | 6/2004 | Rosenfeld | 382/131 |
| 6,754,596 B2 * | 6/2004 | Ashe | 702/56 |
| 2003/0016006 A1 | 1/2003 | Khaflin | |
| 2003/0078502 A1 | 4/2003 | Miyaki et al. | |
| 2003/0120150 A1 | 6/2003 | Govari | |

* cited by examiner

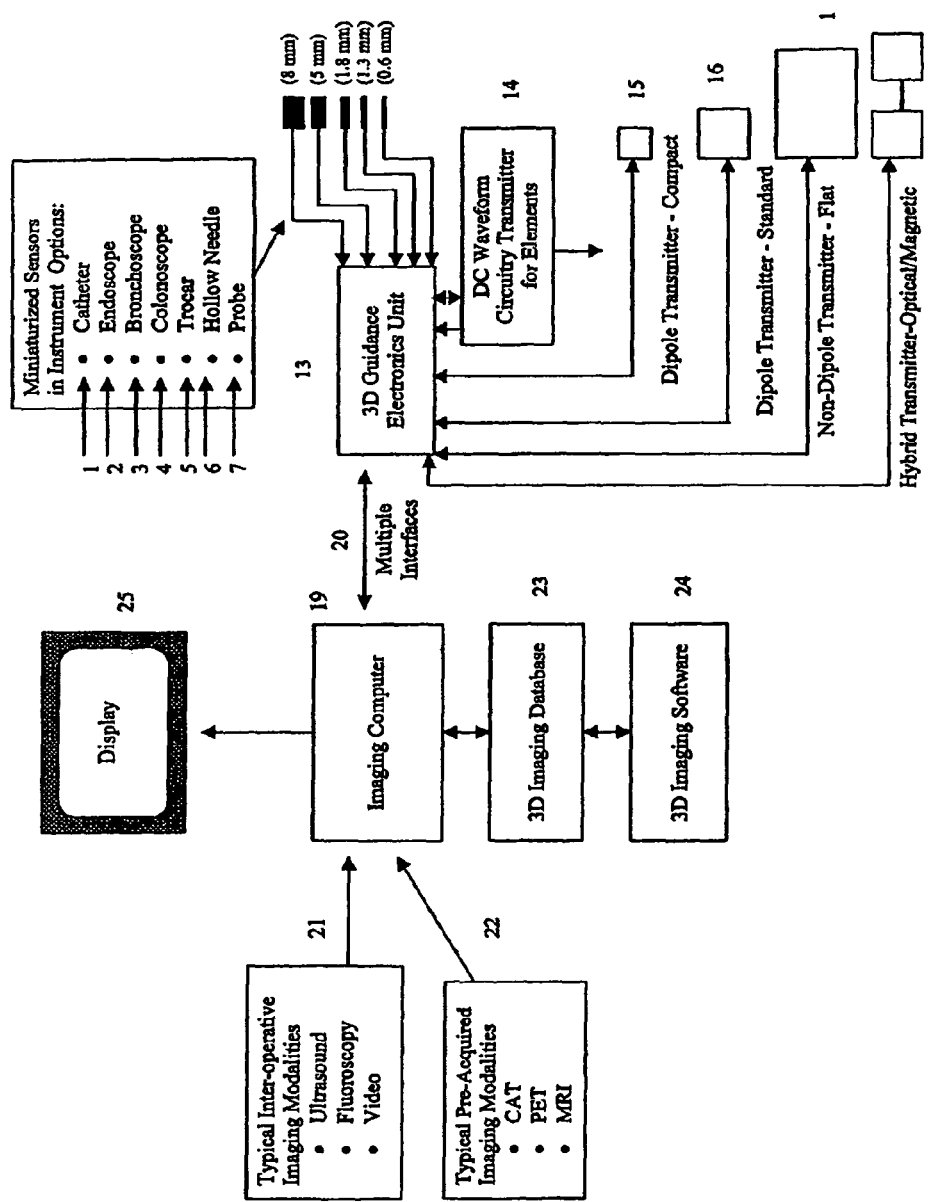
Figure 1. 3D Guidance System for Image-Guided Procedures

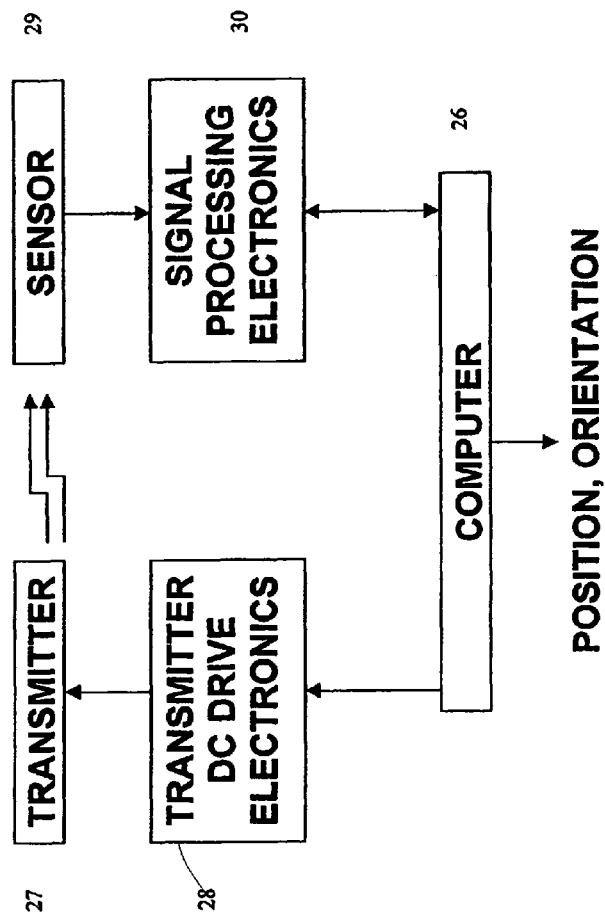
Figure 2. DC Magnetic System Block Diagram

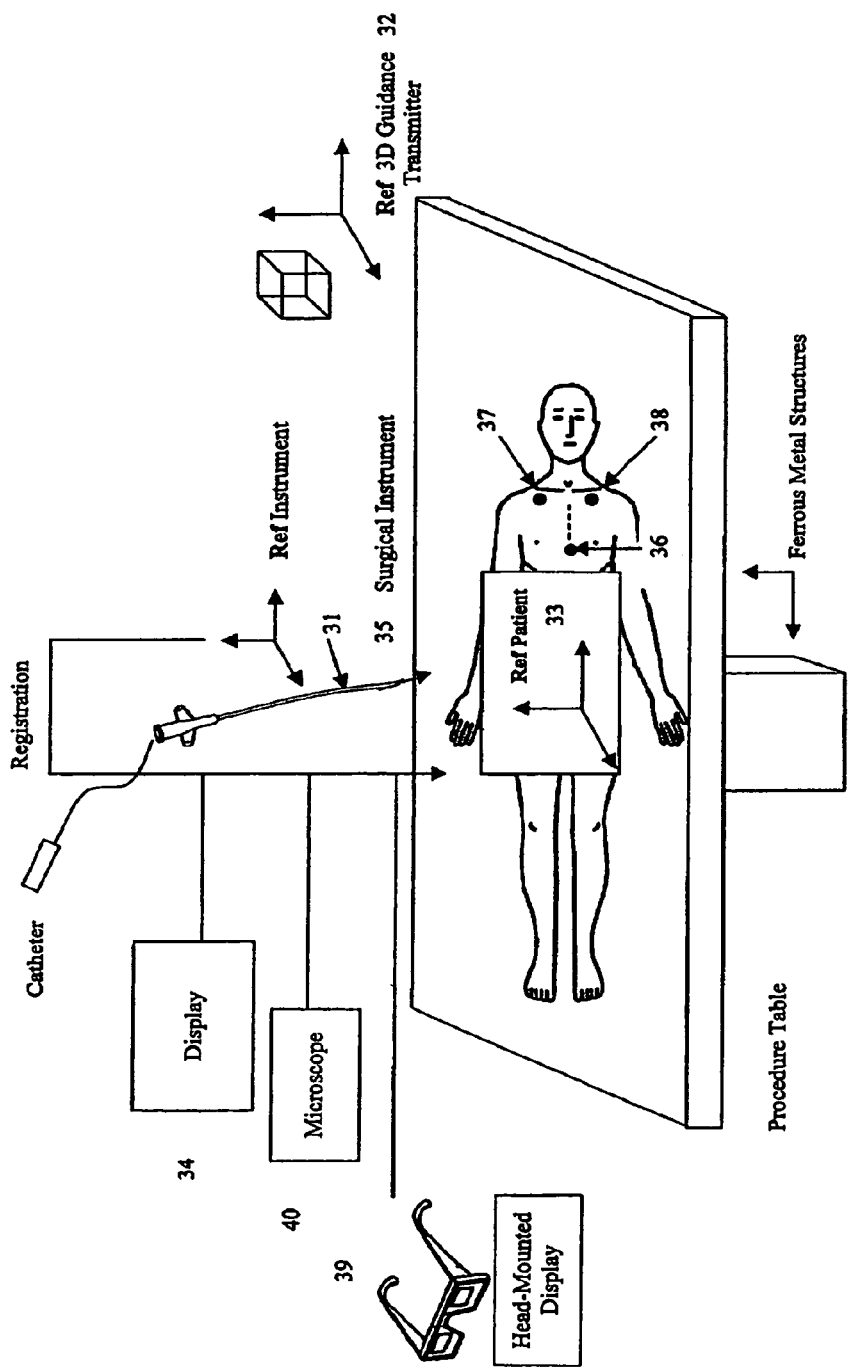
Figure 3. Registration of 3D Guidance System to Patient's Coordinate Reference System

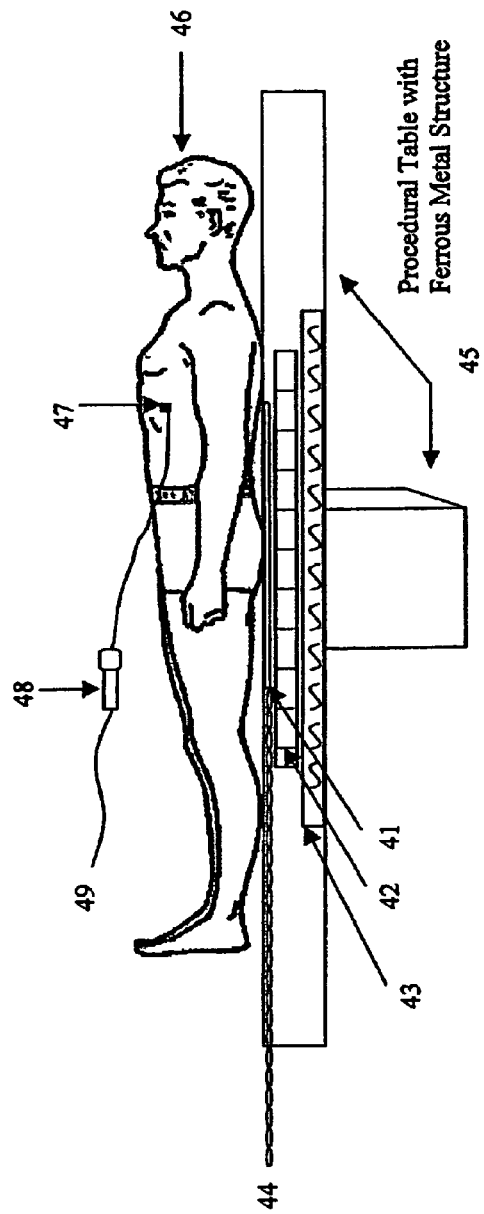
FIGURE 4. Co-Planar Transmitter to Negate Ferromagnetic Distortion of Measurements

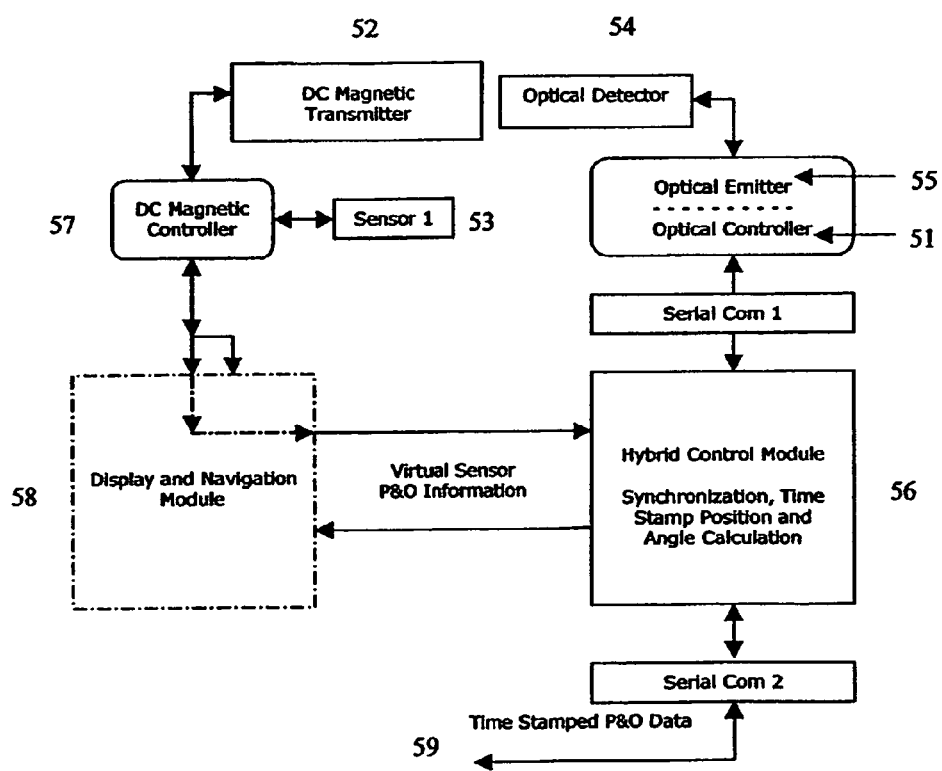
Figure 5. Block Diagram of Hybrid Transmitter

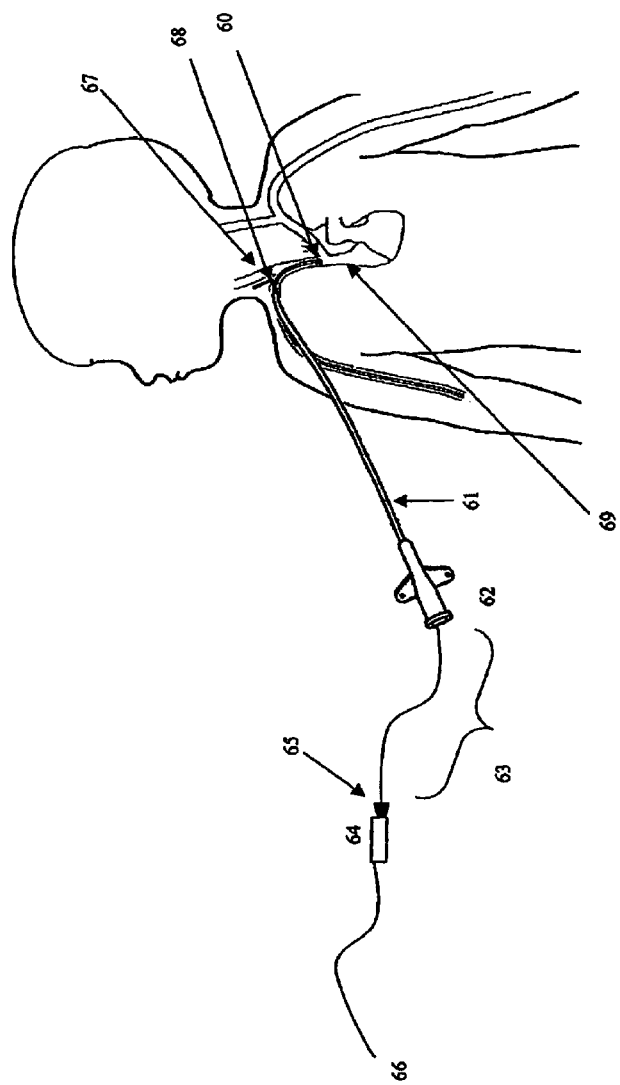
Figure 6. Placement of Micro Sensor into Catheter for Insertion into a Patient

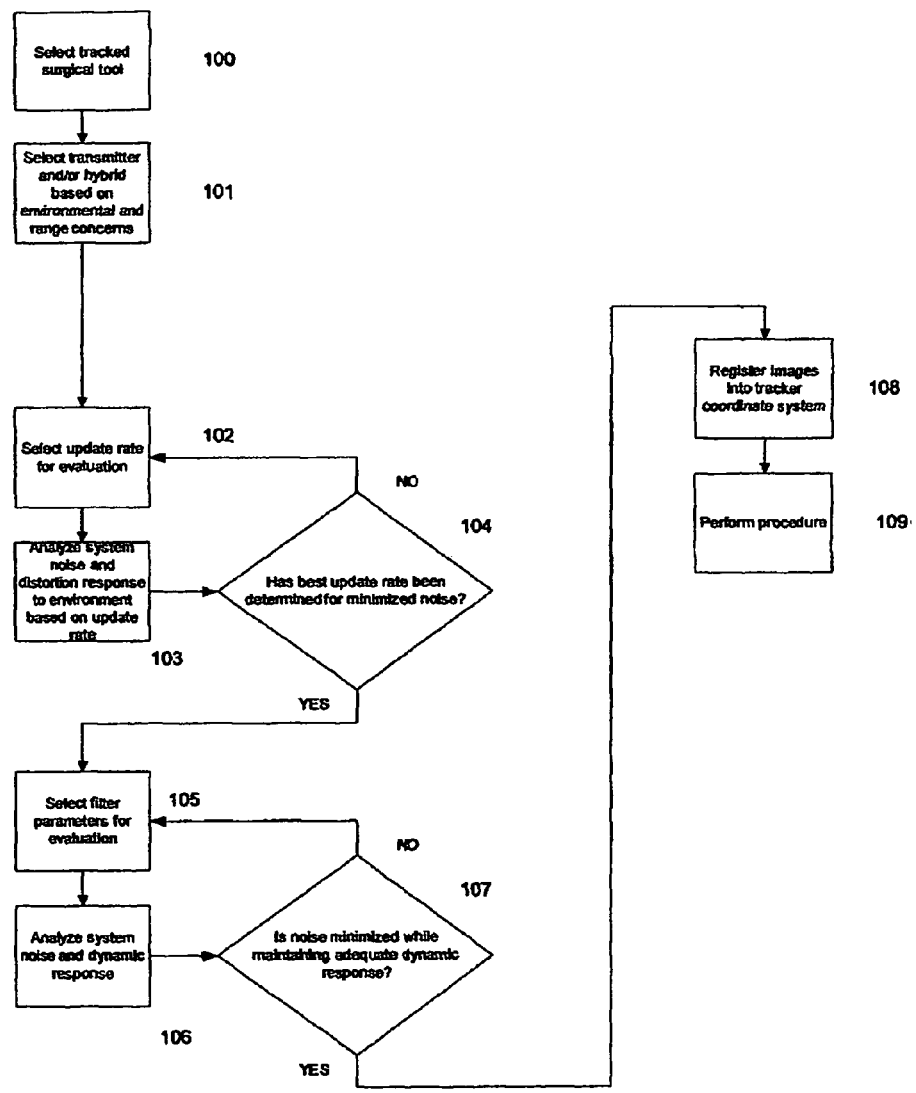
FIG 9. Method for optimizing tracker performance for image guided surgery

DC MAGNETIC-BASED POSITION AND ORIENTATION MONITORING SYSTEM FOR TRACKING MEDICAL INSTRUMENTS

This application is a Continuation of application Ser. No. 11/242,048, filed on Oct. 4, 2005 now U.S. Pat. No. 7,835,785.

BACKGROUND OF THE INVENTION

The present invention relates to a DC magnetic-based apparatus and means to detect—even in the presence of conductive and ferrous metals as well as stray electromagnetic fields—the three-dimensional location of medical instruments within the human body and use this information for guidance purposes in image-guided procedures.

It provides an optimal means of performing electromagnetic guidance within image-guided medical procedures. Based on the principles of pulsed DC magnetic tracking, a panoply of sensors and transmitters is provided to address the requirements of myriad interventional and diagnostic procedures. Procedural requirements commonly include tracking above a metal bed, tracking a catheter inside a patient, and even hybrid tracking methods for localizing miniaturized sensors over the full length of a human body. Once optimal components are selected, system parameters are optimized. These parameters, which directly affect the accuracy, resolution, dynamic performance, and stability of the system, are determined at the time of the procedure. This ensures that environmental factors, including magnetic-field distortion by conductive and ferrous materials and electromagnetic interference, are minimized before the start of the procedure. Optimizations can be performed either manually or automatically.

Minimally invasive, image-guided medical procedures are becoming increasingly commonplace because they reduce patient trauma and costs by condensing both the size of incisions and operating times, they yield better clinical outcomes and reduced hospital stays. The most widespread example is laparoscopic cholecystectomy in which narrow tube-like instruments, holding miniaturized cameras and surgical tools, are inserted through keyhole openings in the abdomen for fast and efficient removal of a diseased gallbladder. In a growing number of minimally invasive applications within organs and vascular structures, however, miniaturized cameras and tools are often insufficient to accomplish the procedure. In these cases, the physician cannot always see where his instrument is located or its direction to a known landmark. Often he must rely on one or more two-dimensional imaging modalities, such as X-rays, fluoroscopy, computed tomography (CT), magnetic resonance imaging (MRI) or ultrasonography. These scans are not aligned to the coordinate frame of the patient and must be mentally stacked together to appreciate the three dimensionality of the patient's anatomy. As a result, guiding instruments to internal targets can become awkward and difficult to achieve when relying on imaging alone. Computer-assisted techniques are often applied to scan planes and render 3D reconstruction of image planes, but they do not solve the 3D guidance problem. The physician is still confronted with the problem of determining where his instrument and his medical target are located in image space. Currently, the most common imaging modality used for instrument guidance is fluoroscopy. While it provides real-time imaging, the results are in two-dimensions only. In addition to limiting the physician's three-dimensional perspective, it further exposes him and patient alike to the health risk of ionizing radiation.

Mechanical, ultrasonic, optical, magnetic resonance, X-Ray, first-generation AC magnetic and second-generation DC tracking technologies have been applied to the image-guidance problem with limited success.

Applicants are aware of the following tracking modalities in the prior art that have been applied to the problem of medical visualization and guidance.

U.S. Pat. No. 4,794,931 to Yock [Cardiovascular Imaging Systems, Inc.: "Catheter Apparatus, System and Method for Intravascular Two-Dimensional Ultrasonography"] discloses an ultrasonic method of achieving high-resolution intravascular imaging, preferably for performing atherectomies. The invention provided an early means of guiding a medical instrument into branches of blood vessels by embedding an ultrasonic crystal in the distal tip of a 9 French catheter, which radiates energy off a reflector into tissue immediately opposite the tip cutout. The resulting ultrasonic image provided a two-dimensional means of visualizing the cross section of a vessel wall for assessing plaque build up and degree of stenosis.

U.S. Pat. No. 5,899,860 to Pfeiffer [Siemens: "Method and Device for Determining the Position of a Catheter Inside the Body of a Patient"] discloses a positional system for catheters. It cannot localize multiple instruments or complimentary instruments such as flexible endoscopes, probes, and long needles. The disclosure broadly identifies a number of energy transmission and reception schemes for localization. Among these are: piezo elements for ultrasonic machines; electromagnetic coils; and Hall-effect generators. The approach is conceptual and does not address real world issues of interference and distortion or the need to find a full six degrees-of-freedom (position and orientation) solution to the localization problem.

U.S. Pat. No. 6,442,417, Shahidi, ["Method and Apparatus for Transforming View Orientation in Image-Guided Surgery"] describes a system and method for increasing the range of motion of an instrument, such as an endoscope, once it is inserted within the patient. The invention enables a physician to increase view orientation for improved observation of an internal target. The patent, does not address the tracking of instruments once inside the body, stating merely that robotic, mechanical, acoustic, optical or magnetic approaches may be applied to navigate an instrument to an internal site.

Mechanical tracking approaches have been applied to the guidance problem. These provide exceptional accuracy but are hampered by cumbersome mechanical linkages that interfere with physician motions and instrument maneuverability. They also have difficulty tracking multiples points and handling sterilization requirements. Their greatest problem is inability to track flexible instruments inside the patient.

U.S. Pat. Nos. 5,383,454 and 5,851,183 to Bucholz, ["System for Indicating the Position of Surgical Probe Within a Head or an Image of the Head"] generally disclose mechanical and optical devices for navigating a surgical probe—in neurosurgery. They are based on a stereotactic frame (U.S. Pat. No. 5,383,454) and an optical scanning technique (U.S. Pat. No. 5,851,183) employed to aim a surgical probe at targets inside the brain, referenced to pre-established coordinate points. Another mechanical approach is an automatic apparatus for computer-controlled stereotactic brain surgery as described in U.S. Pat. No. 5,078,140 to Kwoh. Its needle guide is integrally connected to the stereotactic apparatus, thereby allowing the physician to choose the most suitable trajectory of the needle toward the target. This is a highly-complicated expensive system, requiring recalibration for each procedure.

Optical devices constrain the physician to maintain a clear path (unrestricted line-of sight) between a source of radiated energy (e.g., light or infrared energy emitted from active markers or light or infrared energy reflected from passive markers) and optically sensitive detection arrays, such as charge-coupled devices (CCD). In a busy and crowded operating room, maintaining a clear path between emitting and detecting elements is not always practically possible. Because the emitter or detector is placed on the proximal end of a rigid instrument, the system must calculate an offset for accurate distal tip measurements. This allows errors to creep into the measurements and cannot account for bending of the instrument during a procedure. Also, the lever effect magnifies small errors at the proximal end into large, sometimes unacceptable errors at the distal tip. For flexible instruments (such as catheters and endoscopes) fully inserted within the body, optical tracking devices are impractical.

Optical patents, such as U.S. Pat. No. 5,617,857 to Chader [Stryker: "Imaging System Having Interactive Medical Instruments and Methods"] generally disclose an imaging system in which a medical instrument is tracked by optical means. In this system, light emitting diodes (LEDs) are attached to the instrument referenced to a nearby bank of detectors. The system is connected to a computer display so that the location of the instrument relative to a pre-acquired image of the patient's anatomy can be viewed. Again because a clear line of sight must be maintained between emitters and detectors, it cannot be used to track flexible scopes and catheters inserted inside the body.

U.S. Pat. No. 6,167,296 to Shahidi ["Method for Volumetric Image Navigation"] discloses a computer-driven navigation system connected to a surgical instrument for the purpose of locating instruments in real time and displaying such information on a computer display. It specifies an optical position tracking system employing LEDs and detectors to provide real-time instrument location and means to register images with respect to the patient, and imaging software for reconstruction of 3D images of pre-acquired scans. While an optical system is the preferred embodiment, the inventor states that a sonic tracking system can also be employed. Both approaches require the aforementioned clear line of sight between sources of energy (light or acoustic) and detectors mounted on instruments.

A magnetic resonance imaging (MRI) system is a complex, expensive imaging modality whose signals have been applied to monitoring the position of a specially configured catheter within the body. It has become an attractive approach for research purposes because it offers superior soft tissue contrast and excellent capability for functional testing. Due to the expense, complexity and health issues (i.e., intravascular heating) related to this approach, it has not been used for generalized 3D localization in image-guided procedures.

U.S. Pat. No. 5,318,025 to Domoulin [GE Medical, "Tracking System to Monitor the Position and Orientation of a Device Using Multiplexed Magnetic Resonance Detection"] anticipated the need for 3D instrument localization and developed a catheter containing receiver coils sensitive to magnetic resonance signals. Since detected signals are substantially proportional to the location of the coil along the line of the MRI field gradient, they are used to determine the catheter's position and orientation within the body. This localization procedure requires scheduling time in the MRI suite and cost per procedure is prohibitive for general-purpose image guidance. Other drawbacks include the requirement to inject contrast agents, the need to remove metallic equipment from the MRI suite, and the inability of the system to image from off-axis angles for optimal viewing.

Real time X-Ray technology, i.e., fluoroscopy, is the de facto standard for localization and guidance of instruments within the body. Serious restrictions, as stated above, include: two-dimensional imaging, reliance on use of contrast agents, expense and radiation exposure. Fluoroscopic proponents and critics alike have unanimously called for less reliance on this modality. Once a viable 3D guidance device is fielded for image-guided procedures, fluoroscopy for localization purposes will most likely be limited to calibration and verification of information provided by non-ionizing means.

In addition to these approaches, both alternating current (AC) and direct current (DC) magnetic field generating and sensing technologies have been applied to the medical guidance problem.

For the purposes of categorization, AC magnetic technology and its many derivative implementations are defined as first-generation magnetic tracking. The technology first gained the interest of medical researchers because of its capability to track sensors without line-of sight restrictions, thus enabling trackable sensors to be inserted into the body without occlusion or data loss. Operationally, these systems read induced sensor voltages referenced to one or more magnetic fields and measure near-field magnetic field vectors. Typically one or more magnetic coils in a sensing assembly provide sufficient information to solve its position and two or three angular rotations relative to a dipole transmitter whose two or three coils are sequentially or simultaneously energized. Non-dipole transmitters can also be employed.

First-generation AC electromagnetic tracking is based on transmission and sensing of AC magnetic fields first patented in 1975 (Kuipers, U.S. Pat. Nos. 3,868,565 and 3,983,474) and 1977 (Raab, U.S. Pat. No. 4,054,881). While solving the aforementioned line-of-sight problem of acoustic and optical systems, the technology is acutely sensitive to measurement distortion from common hospital metals, such as electrically conductive metals (e.g., 300-series stainless steel, copper, titanium, aluminum and carbon composites) as well as ferrous metals (e.g., iron, steel and certain nickel alloys). In the presence of these metals, AC field waveforms, which are constantly changing, produce circulatory (eddy) currents in nearby metals that generate secondary fields distorting field patterns. These spurious fields spawn additional sources of magnetic fields resulting in measurement errors in the sensor. To address the restriction of tracking in regions free of conductive and ferromagnetic metals, a number of approaches have been patented to deal with the problem. Among these are: application of mapping and compensation techniques (Raab et al.), implementation of mathematically derived correction factors to measurements (Anderson, U.S. Pat. No. 6,774,624), compensation by measuring and adjusting phase shifts detection metal (Acker et al), shielding of distorters (Anderson—U.S. Pat. No. 6,636,757; Jascob, U.S. Pat. No. 6,636,757), signal processing of eddy current effects (Seiler, U.S. Pat. No. 6,836,745), sounding of warning signals when a distorter is detected (Kirsh, U.S. Pat. No. 6,553,326) etc. Despite the development of these and other AC distortion control strategies, AC systems still require that a physician adopt a number of workarounds and, in some cases, procedural changes to handle the metal problem. These include, among other things, requiring the physicians to use expensive non-metallic instruments and non-metallic operating tables, performing procedures within the confines of large sets of obtrusive coils, engaging in costly and tedious set-up/calibration procedures, and restricting the range and motion of physicians, instruments and equipment.

Representative AC magnetic patents applied to medical imaging include: U.S. Pat. No. 6,233,476 to Strommer et al.

[Mediguide: "Medical Positioning System"]. It discloses a medical device employing an AC magnetic sensor for determining the position and orientation of a surgical probe relative to a reference frame in association with an imaging system. In the preferred embodiment, it claims to overcome the disturbing effects of metal objects by employing a system in which a plurality of electromagnetic fields are generated and sensed. The implementation, however, is costly and subject to numerous transmitter signal pick-up errors by its sensors, which produce noise in outputs and limit its general use in image-guided procedures.

U.S. Pat. No. 6,690,963 ["System for Determining the Location and Orientation of an Invasive Medical Instrument"], issued to Ben-Haim of the Biosense Webster division of Johnson & Johnson is representative of many AC magnetic tracking variations and techniques to achieve 3D magnetic guidance of image-guided procedures.

U.S. Pat. No. 6,836,745 to Seiler [NDI "Method for Determining the Position of a Sensor Unit"] discloses a means of reducing metallic distortion from conductive metals in five degrees-of freedom AC magnetic tracking systems. It claims to correct these distortions by measuring the location of electrically conductive objects and entering this data into a computer program, which calculates the eddy currents and the resulting field distortions. These distortions are then defined in the coordinate system defined by the AC field transmitter and the interference field generated by the eddy currents is nulled. The patent claims that mathematical models are then used to form a correction to the error. In practice, a method that tries to calculate eddy currents as a "virtual source" will yield an overall improvement in reducing distortion but the error is unlikely to reach zero. Such a system also suffers from noise issues if it attempts to overly compensate for the conductive metal. The inventors acknowledge that the system cannot always totally eliminate conductive metal distortion and make no claims to correcting for ferromagnetic metals commonly found in operating rooms.

U.S. Pat. No. 6,636,757 [Medtronic: "Method and Apparatus for Electromagnetic Navigation of a Surgical Probe Near a Metal Object"] to Jascob claims a method and apparatus for AC electromagnetic navigation of a surgical probe near a metal object. It positions a shield near a metallic object in an attempt to reduce field distortion. The chief limitation to this approach is the ubiquity of metal in the operating room. Because the system generates and senses AC fields, multiple obtrusive shields must be instrumented for each procedure. Indeed Jascob acknowledges in his preferred embodiment that the system must shield multiple objects, such as: the operating room table, fluoroscope, microscope, high intensity focused ultrasound system, multiple ultrasound probes, intra-operative CT and MRI machines, surgical robotic equipment, and even metal trays. Further the system assumes that the shielding is placed on metallic objects that remain static or stationary. Once an objects moves, however, it must be recalibrated. This is an unrealistic requirement due to the constant movement of clinicians and equipment as well as contamination rules that demand that nothing be touched or moved in the sterile field around a patient.

U.S. Pat. No. 6,774,624 to Anderson et al. [GE Medical Systems: "Magnetic Tracking System"] offers a theoretical dissertation on a broad range of modeling and shielding techniques to moderate metallic distortion caused by eddy currents in AC electromagnetic systems. In one aspect of the invention, a conductive shield is disclosed, configured to fit about or contain an interfering component or piece of equipment. The shield standardizes the magnetic field disturbance introduced by the component.

To address the metal sensitivity problem of AC magnetic trackers, second-generation technology, employing pulsed DC magnetic field generation and sensing, was first patented in 1989 (U.S. Pat. No. 4,849,692 to Blood) and 1990 (U.S. Pat. No. 4,945,305 to Blood). It provides six degrees-of-freedom tracking while overcoming critical conductive metal distortion deficiencies of first-generation AC magnetic technology. Using a fluxgate, it takes advantage of the steady state of pulsed DC waveforms to measure the field at an instant in time when eddy currents are not being generated in nearby metals. Accurate measurements may therefore be made in medical environments rich in conductive metals. In particular, it is inherently insensitive to medical type metals such as 300-series stainless and titanium, even when operating at a high measurement rate. DC is also capable of driving other conductive metal errors to zero by appropriate measurement rate reduction. In most AC based systems, the eddy current error can only be reduced slightly with decreased operating frequency.

While second-generation DC technology functions well in many medical applications, such as in the 3D localization of ultrasound probes, it faces a number of issues—sensor size and cost, complexity and limited transmitter options—that reduce its effectiveness and applicability in image-guided procedures.

Patented medical applications employing second-generation DC technology include:

Additional U.S. Pat. Nos. 6,626,832, 6,216,029 and 6,604,404 to Paltieli [UltraGuide] were reduced to practice in the UltraGuide 1000 image-guided system. It employed second-generation DC magnetic tracking technology to correlate the location of an ultrasound scanhead tracked with an 8-mm DC sensor and a long needle tracked at its proximal with a second 8-mm DC sensor. The combination allowed the physician to select a point and angle for needle insertion into the patient's body for visually-aided targeting purposes. Because the system was based on second-generation magnetic technology, miniaturized sensors were not available for insertion in the tip of the long needle. Instead a sensor was mounted on the proximal end, thus requiring a calibration procedure to calculate the tip of the needle referenced to the center of the sensor at its far end. Additionally, the system lacked a reliable means of determining whether flexure of the needle occurred during the procedure, since any misalignment of the tip of the needle versus its sensor location results in mis-targeting. Paltieli's U.S. Pat. No. 6,626,832 was developed as a means of detecting the bending of the medical instrument once inserted into the human body. At the time the system was introduced, only a single DC transmitter (not designed for imaging applications) was available. This made it difficult for early Ultra-Guide implementations, which mounted the transmitter in a standoff chassis, to overcome ferrous metal distortion and achieve high accuracy performance.

The present invention addresses these and other critical tracking issues in the prior AC and DC magnetic tracking art that must be solved for 3D guidance to be easily implemented and accepted within the medical community.

It accomplishes this purpose, as explained below, by applying third-generation magnet field generation and sensing technology to the medical guidance problem. By specifically addressing metal and noise—as well as sensor size and cost issues—it offers a significant improvement over current methods of localizing instruments within the human body. Its integration with advanced imaging modalities and imaging software further allows three-dimensional localization data to overcome the inherent limitations of visualizing 3D anatomy with 2D imaging tools.

The application of third-generation magnetic technology will serve many medical purposes. Of primary interest is its capability of synchronizing instrument tip with internal anatomy; of providing 3D reference points superimposed on imaged parts; of mapping and locating anatomical features; of navigating tools to pre-identified locations; of providing instantaneous feedback; and of facilitating the delivery of therapies to targets deep inside the body. Exemplary but by no means inclusive procedures benefiting from third-generation tracking technology include: endograft localization for treatment of abdominal aortic aneurysms, guidance of ablation probes to deep-seated tumors, 3D localization of robotic end-effectors to avoid collisions, in vivo quantitative assessment of pathology and, mapping of locations for implantation of radioactive seeds in soft tissue, 3D guidance for improved visualization in colorectal cancer screening, as well as guidance of diagnostic and therapeutic catheters and probes, such as endoscopes, laparoscopes, colonoscopes and bronchoscopes, to organs and structures within the human body.

SUMMARY OF THE INVENTION

The present invention improves upon the state of the art by providing a general-purpose means of accurately, reliably, cost-effectively and robustly guiding instruments to targets within a patient's body. It accomplishes the purpose by merging recent advances in pulsed DC magnetic tracking technology with advanced imaging technology and minimally invasive techniques.

Because image-guided procedures are performed on different parts of the body and in varied operating rooms—filled with variable medical equipment that can severely distort and interfere electromagnetically with guidance measurements—no one set of components or technologies can accommodate all purposes. For this reason, the novel application of multiple third-generation DC magnetic technologies is required to solve the problem. This includes the integration of multiple transmitter and sensor options as well as the implementation of new electronics, algorithms and signal processing techniques—all readily integrated into existing medical imaging and display systems. The new technology also provides for a low cost, disposable sensor insertable into a catheter—ranging in size from 9 to 3 French equipped with sensors ranging in diameter from 1.8 mm down to 0.6 mm in width—while consistently providing accuracy of measurements in the sub millimeter/degree range.

Multiple DC magnetic transmitters options are provided with the system in orthogonal, non-orthogonal and hybrid modes to maximize accuracy and unobtrusiveness as well as to minimize potential conductive metal and ferromagnetic distortion problems. In addition to a larger transmitter providing tracking range over a cubic meter, transmitters with smaller form factors for close-in guidance at the 10-20 cm range are also provided. For procedures in which ferrous metal is present, a planar (flat) transmitter is provided to negate any effects emanating from metal below the patient. Finally, for procedures requiring sub-millimeter accuracy over an extended range—a new hybrid (DC magnetic/optical) transmitter is provided. New and improved electronics utilizing advanced digital technology and Kalman filtering are further provided to make available a range of performance, interface and data reporting options.

Finally, new and improved hardware is provided whose signal processing capabilities are sufficiently powerful enough to overcome limitations of earlier generation DC magnetic tracking which required compensation for the Earth's magnetic field, significant filtering to reduce jitter in data, and the use of a large flux-gate magnetometer in each sensor assembly to sense transmitted field vectors. For image-guided systems, these limitations have added an unacceptable penalty in additional processing time, sensor size and costs that are instantly overcome with next generation technology.

New and improved noise reduction software is further provided to minimize potential jitter in data caused by the presence of stray magnetic fields that may be present in the operating room, such as caused by power lines, motors, pumps, computer displays and power transformers. If the interfering noise source does not change its frequency, it can be automatically measured by the system, which adjusts its measurement rate to minimize noise effects.

In image-guided interventions, one or more third-generation miniaturized sensors are incorporated into a probe or an elongated tube-like instrument, such as but not limited to a catheter, laparoscope, bronchoscope, colonoscope or endoscope, for insertion through bodily openings or small incisions. In this way, the patient's body may be accessed and procedures performed with minimal invasiveness. A key aspect of image-guided intervention is the ability of the system to register specific 3D points in human anatomy to previously acquired (CT, MRI, PET) or intra-operative (X-ray fluoroscopy or ultrasound) images. These images form a so-called "roadmap" of the inner body with the guidance device acting as a "GPS-like" navigator along the route. Like land-based systems, both the map and the navigational coordinates in an image-guided system must be instantly and accurately viewable on an adjacent high-resolution display. By following the virtual roadmap, a physician can thus guide his instrument to an internal target with precision while avoiding danger spots, such as ducts, nerves and major blood vessels.

Medical imaging software, such as, but not limited to, Cedara Software Corporation's Vivace (Mississauga, Canada; www.cedara.com)—a collection of 2D and 3D visualization software programs—is commercially available for use in image-guided systems. It allows imaging-system developers to build a visual system in which structures can be viewed as volume renderings, segmented and clipped for identification of critical sites, re-formatted for multi-planar viewing, and isolated for detailed analysis.

Once this or similar software is integrated with the 3D guidance device, a physician can use its outputs to identify the position and orientation of one or more reference points, often tagged with radiological opaque markers, on anatomical landmarks on the patient. These markers are visible on image scans of the patient and their coordinates entered into an imaging database. At this point, these scans are not registered or aligned with the patient's coordinate reference frame or the physician's viewpoint of the anatomical target. The goal of image-guided procedures is to provide the physician in the operating or procedural room with computer-assisted view of the scans that are registered with the patient's coordinate reference frame and his view of the patient's anatomy.

Registration is accomplished by a number of means, well known in the art. (See J. B. Antoine Maintz and Max A. Viergever, "A Survey of Medical Image Registration," Medical Image Analysis, (1998), Volume 2, Number 1, pp 1-37, Oxford University Press, Image Sciences Institute, Utrecht University Hospital, Utrecht; J. B. Antoine Maintz and Max A. Viergever, "An Overview of Medical Image Registration Methods," Imaging Science Department, Imaging Center Utrecht, 1996; J. West, J. Fitzpatrick, M. Wang, B. Dawant, C. Maurer, R. Kessler, and R. Maciunas, "Comparison and Evaluation of Retrospective Intermodality Image Registration Techniques," Proceedings of the SPIE Conference on Medical Imaging, Newport Beach, 1996; and C. R. Maurer, Jr. and J. M. Fitzpatrick, "A Review of Medical Image Registration," Interactive Image-Guided Neurosurgery, R. J. Maciunas, Ed., pp 17-44, American Association of Neurological Surgeons, Park Ridge, Ill. 1993.) Many registration algorithms, based on touching multiple fiducial points in image space (reference frame #1) and patient space (reference frame #2), are available for solving the registration problem, including the method described by C. Maurer, et al., "Registration of 3-D Images Using Weighted Geometrical Features," IEEE Transaction on Medical Imaging, Vol. 15, No. 6, December 1996, incorporated herein. Some of the most effective techniques accomplish the purpose by directing the physician to place the tip of the instrument on "fiducials," i.e., anatomical landmarks or markers affixed to the patient. These data are then used in an algorithm, resident in the imaging software, to perform appropriate coordinate transformations and align image space to patient space, thus mapping the corresponding fiducials from one reference frame to another. A properly constructed registration algorithm accounts for shifts, rotations and scaling of points form one frame to another. The algorithm provides for a tight registration between frames with minimal errors between scanned images and targets. From this point on, the patient's anatomy is correlated to the image data. The imaging software can now display the position of the instrument's tip in the patient to its corresponding position in the image and visa versa. In many procedures, instruments are tracked on interactive displays, adjacent to the operational field or even displayed on a head-mounted display. Such displays allow the physician to see anatomy through a stereoscopic "window." In this way, as an instrument's distal tip is moved toward an internal target, the physician sees a high-resolution, full-color stereoscopic rendering of the patient's anatomy and the trajectory to an internal target.

It is a first object of the present invention to provide a new and improved means and apparatus for 3D guidance of instruments in image-guided medical-surgical procedures. The improvement comes from the use and integration of third-generation pulsed DC magnetic tracking technology that is highly adaptable and amenable to a wide range of medical procedures. The invention provides for a general-purpose system that operates inside an operating room with significantly smaller measurement errors than prior art systems, all of which are compromised in one way or another by performance limitations of the technologies employed or by deficiencies caused by their implementation in a medical environment.

Another object is to provide a new means of reliably guiding medical instruments to targets within the human body without worrisome issues of metallic distortion of measurements, noise interference, high cost of sensing elements, reliance on less than optimal error-correction techniques and the overriding limitation of non-robust performance due to environmental constraints.

Another object of the present invention is to provide a new and improved means of tracking the distal, midsection or proximal tip of one or more medical instruments with one or more miniaturized sensors, the position and orientation of which is referenced to one or more transmitters emitting pulsed DC magnetic fields waveforms and not affected by conductive or ferromagnetic metals in the medical procedural room. Such sensors must be sufficiently small enough to be inserted into the tip of instruments, such as biopsy needles and ultra-thin probes/scopes, to overcome the so-called "needle bend" problem.

Another object of the present invention is to use pulsed DC magnetic fields to instantly and precisely track the tip of an instrument registered to one or more imaging modalities to provide a physician with images correctly aligned with the coordinate reference frame of the patient.

Another object is to provide an instrument position and orientation determination system without placing artificial constraints on the relative position of the medical instrument, composition of the instrument, and/or the room in which the procedure is performed.

Another object of the present invention is to track the distal tip of a catheter capable of being inserted into the vascular system or urethra for 3D localization and mapping purposes.

For practical implementation, it is also necessary to provide a system that is integrated with imaging software so that anatomical imagery can be referenced in the patient's frame of reference and viewed in a clear and intuitive fashion.

Yet another object of the present invention is to overcome the deficiencies of first-generation AC and second-generation DC magnetic systems employed in image-guided procedures. Most importantly, for 3D guidance in an image-guided procedure, the ferromagnetic issue must be addressed. Practical systems must perform robustly in the presence of these metals, commonly found in hospital operating rooms and surgical procedure tables. Third generation magnetic technology solves this problem by providing a padded planar transmitter, upon which the patient lays. It contains a permeable shield that prevents metal objects in the procedural table and beneath it from interfering with the fields generated above the patient. In addition to the ferrous metal issues, third-generation DC magnetic tracking presents a new generation of non-fluxgate sensor technology. It instantly overcomes critical issues, including: sensor noise induction from its transmitter, cable impedance, power-line induced noise interference, component mis-matching, and over-sensitivity to cable and cable conditioner bandwidth issues. In the prior art, these issues all produced critical error sources when magnetic technology was asked to operate with miniaturized sensors and unconventional cable geometries in hospital environments.

It is yet another object of the present invention to overcome disposability and cost issues currently associated with 3D guidance devices by making available a family of miniaturized sterilizable sensors for insertion into the tips and members of instruments and capable of one-time, low-cost use in high volume procedures.

BRIEF DESCRIPTION OF THE DRAWINGS

FIG. 1 is a block diagram of the 3D guidance system for image-guided procedures.

FIG. 2 is a schematic drawing of the pulsed DC circuitry provided in the 3D-guidance system to overcome metallic distortion.

FIG. 3 is a schematic drawing illustrating the coordinate transformations implemented to register 3D coordinate reference frame of an instrument viewable on an interactive display within a patient's coordinate reference frame.

FIG. 4 is a side perspective view showing the location of a co-planar transmitter with permeable barrier beneath a patient lying on an operating table.

FIG. 5 is a schematic drawing of a hybrid transmitter system for providing high accuracy guidance over an extended range.

FIG. 6 is a schematic of the manner in which a miniaturized DC magnetic sensor is inserted and controlled inside a catheter.

FIG. 9 is a flow chart of the overall method of optimizing tracking performance for image-guided surgery.

DETAILED DESCRIPTION OF THE PREFERRED EMBODIMENTS

Figure 7A:
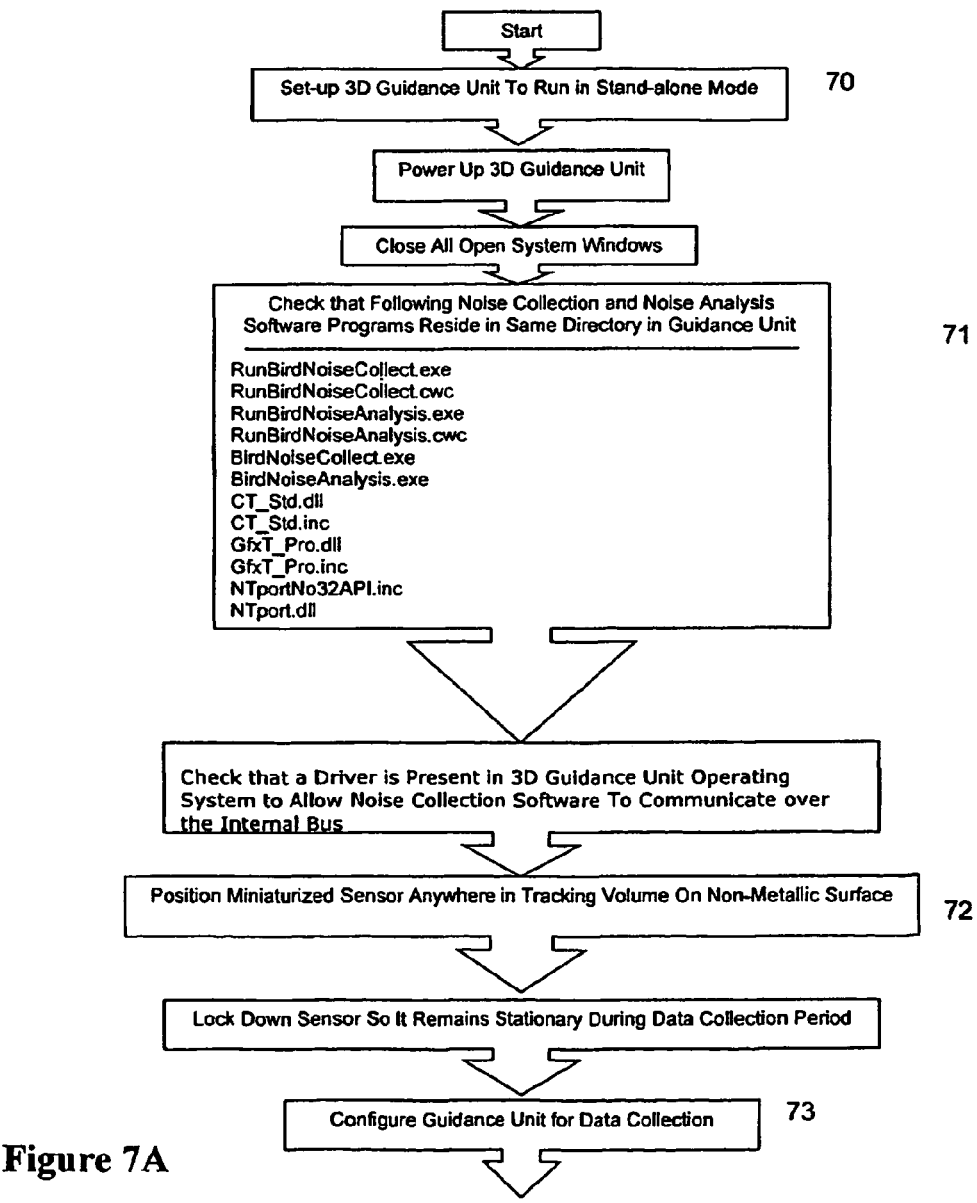
FIGS. 7a, 7b and 7c combine to show a flow chart for implementing noise reduction software to minimize data jitter in a medical operating room.

FIG. 1 presents an exemplary embodiment of the DC magnetic guidance system for image-guided medical procedures. A representative example of the DC tracking portion of the guidance system is detailed in U.S. Pat. No. 6,754,596 to Ashe, which is assigned to the assignee and incorporated herein by reference. The system includes a freely moving medical instrument, by which is meant all manner of surgical tools and devices for use in medical treatment. It is typically initialized for computer use as one or more of the devices, identified by the reference numerals 1, 2, 3, 4, 5, 6 or 7, namely, such as a catheter capable of being inserted within a patient's body through the skin, bodily orifice or incision. It permits targeting of an anatomical organ, structure or vessel for visualization, diagnostic and/or interventional purposes. Such instruments are typically thin, elongated and flexible, containing a proximal end for control by the physician and at the distal end, a DC sensor assembly 8, 9, 10, 11, or 12 is embedded in the tip of a working channel. The particular sensor assembly is determined by the procedure type and measurement performance requirements. Ultra thin cables connect the sensor(s) with breakaway connectors to an electronics unit 13, 14 taking the form of either a stand-alone electronics unit or one or more electronics cards. As shown in FIG. 1, the sensors are miniaturized, preferably ranging from 8 mm to 0.6 mm in width and may be further shaped and dimensioned to fit procedural requirements. Of novel importance is that fact these DC magnetic sensors are impervious to conductive, low-permeability metal distortion and noise interference. When used with a flat transmitter, they are also immune from permeable metal distortion emanating from ferromagnetic objects beneath the patient. They are similarly free from error sources related to cross coupling, cable impedance, component matching, and signal conditioner bandwidth issues. Multiple miniaturized sensors may also be placed at instrument segments, as well as on adjacent anatomical structures for respiratory or cardiac gating purposes. Placement and dimensions again will depend on the procedure and parameter to be measured. Under control of circuitry for energizing DC magnetic fields 14, each sensor(s) measures its instantaneous position (X, Y, Z) and orientation angles (Yaw, Pitch and/or Roll) in three-dimensional space referenced to the transmitter element chosen for the procedure. Examples, but by no means all transmitter assembly options for generating the fields are referred to by reference numerals 15, 16, 17 and 18. Like the sensor element choice, the transmitter element is determined by the procedure and the parameter to be measured. The transmitter element is typically fixed in space beside, above or beneath the patient or on medical equipment, where it acts as the reference frame for the measurements. In the case of the co-planar (flat) model 17, it also effectively functions as a means and apparatus to negate the effect of ferromagnetic distorters beneath its surface, such as procedural tables and equipment. When integrated with the imaging system, these measurements provide sufficient information to navigate an instrument within the body for diagnostic and interventional purposes.

The imaging computer 19, typically incorporating a personal computer running a current operating system and mounted in a portable chassis, is connected to the guidance electronics unit by one or more interfaces 20, such as RS-232, RS-422, USB, Firewire or Ethernet. Its network protocols are designed for sending and receiving configuration data and responsiveness to communications, synchronization and performance commands sent it by the imaging computer.

The imaging computer further stores pre-acquired 21 or intra-operative 22 images of the patient in its 2D and 3D imaging database 23, which are then input to 3D imaging software 24 for registration and visualization purposes. During the medical procedure, the three-dimensional location of the chosen instrument(s) 1, 2, 3, 4, 5, 6, and/or 7 is tracked relative to the patient's anatomy and the pre-acquired or interoperative images and shown in real time on a display 25, of the imaging computer 19. When the medical instrument is advanced toward the target of interest within the patient's body, the transmitter element 15, 16, 17, or 18 is activated and energized thus producing measurable voltages in the specified sensor assembly 8, 9, 10, 11, and/or 12 connected to the guidance electronics unit. At the guidance electronics unit 13, these voltages are processed and the 3D location computed for immediate transmission to the imaging computer 19.

Before the start of the procedure, at least two protocols are implemented. The first initializes the specific instrument and sensor assembly that will be tracked by the imaging computer. Configuration data, such as instrument type, part number, X, Y, Z sensor location in the instrument, calibration data etc. are stored in the imaging computer's memory 19. From this point forward, the system automatically provides the imaging software with specific configuration of the attached medical instrument. No manual entry of medical instrument data by the physician is required. The second protocol typically correlates the instrument, imaging modality, and patient reference frames so that the physician can guide his instrument intuitively within the patient by following 3D visualization cues. (See FIG. 2 for a detailed description of this protocol.) Once these protocols have been accomplished, the imaging computer 19 can continuously receive instrument guidance data at the patient and align it with locations on the imaging display 25. In this manner, as the physician moves the instrument to a target within the body, he also sees an image on the display of a 3D cursor (or similar icon) of the instrument tip or segments thereof (1, 2, 3, 4, 5, 6 or 7) relative to target images of the patient. Control of the guidance data and integration with scanned images is a function of the 3D software 24 operable on the imaging computer 19. Real-time medical software programs, such as the aforementioned Vivace (commercially available form Cedara Software Corporation) present data through a graphical user interface that contains reconstruction algorithms for volume rendering and manipulation. Critical capabilities include segmentation, reformatting of image slices, clipping of undesirable information, fusion of multiple volumes, true distance and angle measurements, as well as superposition of a cross hairedposition icon on sagittal, coronal and coronal image slices. In this way, a physician can establish a trajectory and movement path to the internal target within the patient's anatomy.

FIG. 2 is a schematic representation of the 3rd generation pulsed DC magnetic transducing technology employed in the preferred embodiment for application to image guidance, as detailed in U.S. Pat. No. 6,754,596 to Ashe and incorporated herein by reference. Under computer 26 command and control, a transmitter 27 has each of its axes energized by DC drive electronics 28 to transmit symmetrical, sequentially excited, non-overlapping square DC-based waveforms. These are received through the air or tissue by a sensor 29 that conveys these signals to signal processing electronics 30. The computer 26 contains an integrator for measuring rising edge and steady state of each axes' sequential waveform so that an integrated result may be measured at the end of the steady state period. It further controls the transmitter DC drive electronics 28 to operate the transmitter and receives signals from the signal processing electronics 30 for the signal integration process, the end result being calculation of the sensor's position and orientation in three-dimensional space with significantly reduced eddy current distortion while providing improved compensation for sensor drift with respect to the Earth's stationary magnetic field and power-line induced noise.

Specifically, the transmitter DC drive electronics or signal generation module 28 includes means for providing or producing pulsed DC current signals of known amplitude to each transmitter axis. The computer 26 sets the current amplitude for each transmitting element. The transmitter, which may be a dipole or non-dipole form, is configured to work near or beneath the patient undergoing the procedure. The sensor(s) 29 measures the position and orientation of the distal tip or segments thereof of the medical instrument and/or is attached to the patient's body for reference or gating purposes. In the preferred embodiment, the transmitter 27 consists of either a three-axis magnetic field generator in which the coils are mutually orthogonal or are co-planar. The system is sufficiently versatile enough to accommodate other transmitter configurations and form factors depending on the medical procedure and the amount of conductive and ferrous metal in the nearby environment. In each case, the system computer 26 is pre-programmed to accommodate the required configuration.

The sensor(s) 29 is also preferably one, two or three-axis coils with mutually orthogonal windings. The sensor is typically mounted in the distal tip or segments along the shaft of the medical instrument that must be guided or localized to an internal target within the patient or localized within the anatomy. The sensor detects DC magnetic fields generated by the transmitter and its outputs are preferably conveyed to receiving means comprising the signal processing electronics or 3D guidance electronics unit 30. The electronics control conditions and converts sensor signals into a digital form suitable for further processing by the computer 26 and computation of position and orientation measurements.

FIG. 3 depicts the manner, under control of the imaging computer, in which the coordinate frames are matched so that a medical instrument, tracked by the DC magnetic sensor, can be registered to the imaging and patient coordinate reference frames. Once accomplished, the physician can intuitively guide the instrument within the patient by following visual cues on an imaging display 25, 34 and/or 39. The process includes running a rigid-body transformation algorithm, well known in the art and incorporated in "prior art references" discussed herein. In conjunction with image processing techniques, it is used to establish a relationship between the coordinate systems of the medical instrument 31, the DC magnetic field transmitter 32 and the patient, 33. One or more registrations algorithms, based on identifying artificial landmarks (fiducials or markers), or anatomical landmarks (skeletal structures) can be employed. Correlating image space 34 (i.e., the 2D view of the patients' anatomy derived by an imaging modality, such as a CAT scanner) and patient space 33 is typically but not exclusively accomplished by first placing the tip of the instrument 35 on anatomical landmarks such as 36, 37, 38 on the patient matched to similar points previously marked on the scanned image. These data are then used to perform appropriate rotational and translational transformations to align image space to patient space. In practice, corresponding fiducials are mapped from one reference frame to another. A properly constructed registration algorithm accounts for shifts, rotations and scaling of points from one frame to another. The algorithm provides for a tight registration between frames with minimal errors between scanned images and patient points of interest. From this point on, the patient's anatomy 33 is correlated to the image data. The imaging software can now graphically relate the position of the instrument's tip within the patient to its corresponding location within the imaged data and visa versa. In many procedures, instruments are tracked on an interactive display 34, adjacent to the sterile field or on an intra-operative microscope 40 or even a stereoscopic head-mounted display 39. In all cases, data are presented graphically and intuitively so the physician can instantly see an instrument's pathway, present and projected, as it moves towards an internal target.

FIG. 4 shows a side view of the co-planar transmitter assembly for overcoming ferromagnetic distortion of the 3D guidance sensor. A representative embodiment of the co-planar transmitter is detailed in U.S. Pat. Nos. 6,246,231, 6,528,991 and 6,784,660 issued to Ashe, assigned to the assignee, and incorporated by reference herein as well an additional co-pending patent application to Schneider, to be assigned to assignee herein. In the Ashe configuration, it comprises a co-planar rhombic transmitter 41 located above a permeable barrier 42 mounted on top of a conductive plate 43. The transmitter 41 itself consists of a printed circuit card with loops etched in three axes onto its surface. The permeable barrier 42 is made of a highly permeable non-conductive material. Depending on the distorter to be shielded, it is typically composed of ferrite or mu metal—although other materials and layering schemes may be specified depending on procedural requirements as one skilled in the art will readily appreciate—and located about the transmitter. In operation, the barrier causes the magnetic field to travel primarily upward, effectively shielding objects below the barrier material from distorting sensor measurements. Once energized, the transmitter 41 amplifies the field in the operating region above the table and reduces the field next to the transmitter and below the surface of the operating table. In this way, the 3D guidance system can operate with full assurance that ferromagnetic structures, the bane of real time operation of all previous magnetic tracking devices, will not affect the procedure.

Transmitter circuitry, driven via an electrical conductor 44 to transmitter DC drive electronics 28 of FIG. 2, produces a sequential excitation of each loop with DC current. For 3D guidance procedures, a mu metal barrier is most often chosen because it provides significantly lower vector dilution and significantly higher transmitter field strengths in the volume above the plate. Once placed on the operating table 45 with a patient 46 lying on the padded transmitter assembly (typically 8 to 18 mm thick), a miniaturized sensor 47 embedded in the instrument, such as the catheter 48 shown in FIG. 4, can be accurately tracked even in the presence of a cantilevered operating table 45 supported by highly permeable steel structures.

The sensor 47 receives induced voltage signals from the transmitter assembly 41, which are proportional to the magnitude of the magnetic field and the cosine of the angle between the direction of the magnetic field and the sensor axis, in each of its multiple coils. As one skilled in the art will readily understand, these signals can be amplified and conveyed to the guidance computer FIG. 1, via the electrical conductor 49 connecting the sensor assembly to the guidance electronics unit. Here an active or passive signal processor removes "out of band" signals from corrupting data and adversely affecting the accuracy of the measurement. Additional signal processing adjusts gain states, as necessary, and the signal is further conditioned and multiplexed so that each coil signal is distinguishable from one another before analog to digital conversion, amplification, and input to the guidance unit processor for noise filtering of the digital waveforms. The data are then input to any number of algorithms, such as U.S. Pat. No. 4,287,809 or U.S. Pat. No. 4,314,251 and/or numerous variations in the public domain, readily available for customization and implementation by one skilled in the art. The net result is the solution of a set of non-linear equations yielding the instant position and orientation of the sensor in three-dimensional space and output to the imaging computer.

FIG. 5 shows a block diagram of a hybrid tracking system (magnetic and optical technologies integrated together) for high precision guidance of a miniaturized sensor without loss of accuracy when performing certain medical procedures in which it is prudent to keep the transmitter-to-sensor separation close at all times. It is also useful for vascular procedures requiring high accuracy tracking over an extended range, such as the length of a lower limb bypass graft or the approach to an abdominal aortic aneurysm. A representative embodiment of a hybrid tracking system is detailed in "Extended Range Tracking for Remote Virtual Reality-aided Facility Management" by Zetu and Banerjee, and incorporated by reference herein. The paper was presented at the NSF Design and Manufacturing Grantees Conference in 1998.

In such a hybrid system, DC magnetic and optical subsystems are integrated together so that the optical device 51 constantly tracks and registers the coordinate reference frame of the magnetic tracker's transmitter 52. This enables the physician to conduct the guidance procedure in a very small operating volume, or motion box. Typically, an unobtrusively small, short-range transmitter 52 and its accompanying sensor 53 will never be more than 10 centimeters apart. As long as this minimal separation can be maintained, extraordinary accuracies, in the range of 0.1 to 0.3 mm of a true measurement, are achievable. In the event that the magnetic transmitter 52 must be moved, effectively changing its coordinate reference frame, its position and orientation are tracked by the optical tracking device's detector 54 whose emitter 55 is sufficiently removed from the operating region and of sufficient range so that it remains stationary during the procedure. Thus, reference frame #1 of the magnetic transmitter 52 can be precisely aligned with reference frame #2 of the moved magnetic transmitter 52 and so forth until the procedure is completed.

As seen in FIG. 5, during a power up sequence, a PC-based hybrid control module 56 queries a DC magnetic tracking controller 57 and an optical tracking controller 51 for their calibration data (reference and remote coordinate frame alignments, calibration parameters, etc) and configures both trackers to synchronized configurations (measurement rates, output data formats, digital filters etc.). Once completed, the run-time portion of the system can begin. The DC magnetic guidance controller 57 drives three sequential excitation states of the DC field transmitter 52 that induces measurable voltage changes in the three-axis DC sensor 53. The magnetic controller 57 as described in FIG. 5 processes said changes. Similarly, the optical emitter 55 (co-housed in the optical controller assembly) produces optical signals received by the optical detector 54 that are processed to solve its five or six degrees-of-freedom location referenced to the emitter 55.

At this point, the optical and magnetic trackers collect data independently of one another at their optimal operating rates. However, the optical electronics unit 51 also collects raw data from the DC magnetic controller 57 along with data time stamps. The time stamps let the system synchronize a particular measurement to the instant of time when that measurement was taken. A Kalman-filter based algorithm, working in conjunction with the magnetic tracker position and orientation algorithm, also runs in the hybrid control module 56. The Kalman or similar filter reduces the position and orientation uncertainties resulting from the magnetic trackers time skew effects. Such a filter is described in "SCATT: Incremental Tracking with Incomplete Information," TR96-051, Gregory Welch, October 1996, Department of Computer Science, University of North Carolina, Chapel Hill, N.C., and incorporated herein by reference. In addition, it filters out micro motions, caused by environmental factors, such as vibrations and external noise sources, in both trackers.

Next, the hybrid control module 56 re-samples the optical and magnetic trackers' position and orientation data streams to yield a unified output rate. This step aligns the two trackers data in a manner that allows both outputs to correspond to the same instant of time. Consequently, the optical and magnetic tracker's individual position and orientation data streams can be merged or fused into the hybrid position and orientation solution that describes position and orientation of the magnetic sensor 53 relative to the optical tracker's fixed reference frame 51. Only now can the integrated position and orientation data stream be transmitted to both the display/navigation module for real-time display and to an host imaging computer (not shown) via a common interface 59 for use by imaging computer, as described in FIG. 1.

FIG. 6 shows a miniaturized sensor 60 disposed in the distal end of a flexible catheter 61, similar in construction to that described in U.S. Pat. No. 5,769,843 to Abela et al. It contains a cylindrical channel extending lengthwise therein with an opening at its proximal end 62 for insertion and removal of the disposable sensor assembly and its accompanying cable 63 as well other medical tools necessary to accomplish its purpose. Typically the sensor and cable with connector arrive for single (disposable) use in a sterilized package. The full assembly is typically 40-50 cm in length terminating at a connector insertable into a system pre-amplifier 64. At this point, the disposable version of the sensor can be disconnected from the pre-amplifier's connector 65. The pre-amplifier assembly 64 and its permanent cable 66 always remain connected to the 3D guidance electronics unit (not shown in FIG. 6) but described in FIG. 1. Depending upon the procedure and the age/sex of the patient, catheters ranging in diameter from 1 French (1 mm-wide) to 34 French (11.3-mm wide) are deployed. For vascular procedures, catheters on the smaller end of the scale are always required. To accommodate varying catheter diameters, multiple-sized sensors are provided, ranging from a 8 mm wide assembly to fit within a 26 French catheter down to 0.6 mm wide assembly to fit within a 3 French catheter, as shown in FIG. 1.

Procedurally, a catheter may be introduced into the human body for diagnostic and therapeutic purposes at multiple entry points, such as large veins in the groin, arm or chest. Referring again to FIG. 6, we see for descriptive purposes only a procedure for insertion of a catheter into a chamber of the heart. Following a small incision in the skin near the collarbone 67 exposing a major vessel 68, such as the superior vena cava, a similar incision, creating a tunnel between the surface of the skin and the inside of the vessel, is created. The catheter 61 can now be passed through the tunnel and gently threaded into the vessel toward its internal objective within the heart 69.

By contrast, in the prior art, the physician would track the course of the catheter and monitor insertion problems—such as a looping of the catheter at a "Y" or "J" junction in the vascular system—by watching a X-ray fluoroscope that displays the vessels and the catheter on a 2D viewing screen.

Once the catheter has reached its destination, the physician performs the pre-planned procedure. The continuous fluoroscopy step can now be eliminated or reduced in duration because the physician can now continuously monitor the location of the tip of the catheter as represented by a 3D icon superimposed on the imaging display of pre-acquired or real time patient scans, FIG. 1.

Once the tip of the catheter 61 reaches its target and its three-dimensional location is notated or "locked down" at a specific, X, Y, Z, Yaw, Pitch and/or Roll location, it can be used for any number of treatments. If the catheter contains more than one lumen or chamber, another device can be inserted through the free lumen for diagnostic purposes (such as sampling or biopsy), for interventional purposes (such as cutting, ablating, or deploying special devices. i.e., balloons, baskets or suction devices), or for delivery of agents (such as medications or fluids) to that precise location within the organ. Oftentimes, more than one catheter-based procedure will be performed during the same intervention. Similarly, the catheter can be moved and locked down to a new location for further treatment. For future reference and intervention, the catheter can be repeatedly returned to the same X, Y, Z, Yaw, Pitch and/or Roll location. As those skilled in the art will appreciate, the procedure can be reliably performed without changing established medical protocols to minimize interference and distortion issues. As described hereinbefore, the availability of multiple miniaturized DC sensor options and multiple DC transmitter options overcomes all serious drawbacks prevalent in the prior art.

In FIG. 6, we see the miniaturized sensor 60 threaded through a flexible catheter 61. This represents one method only of introducing the 3D localization and navigation device's guidance sensor into a patient. As will be obvious to those skilled in the art, the sensor family, as shown in FIG. 1, can be embedded, attached or threaded through any number of medical instruments including, but not limited to catheters, endoscopes, bronchoscopes, colonoscopes, trocars, various needles, and probes for non-invasive as well as invasive interventions in all parts of the patient's body.

Figure 7B:
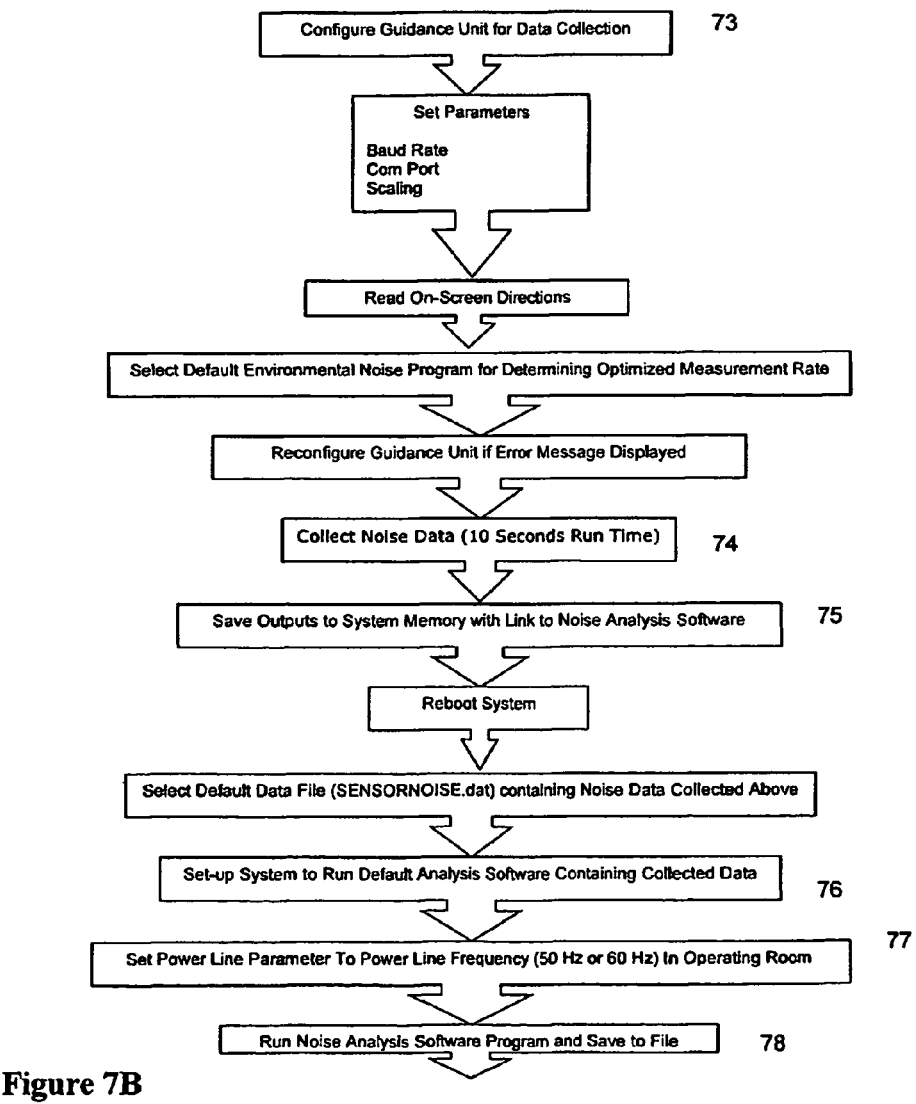
Figure 7C:
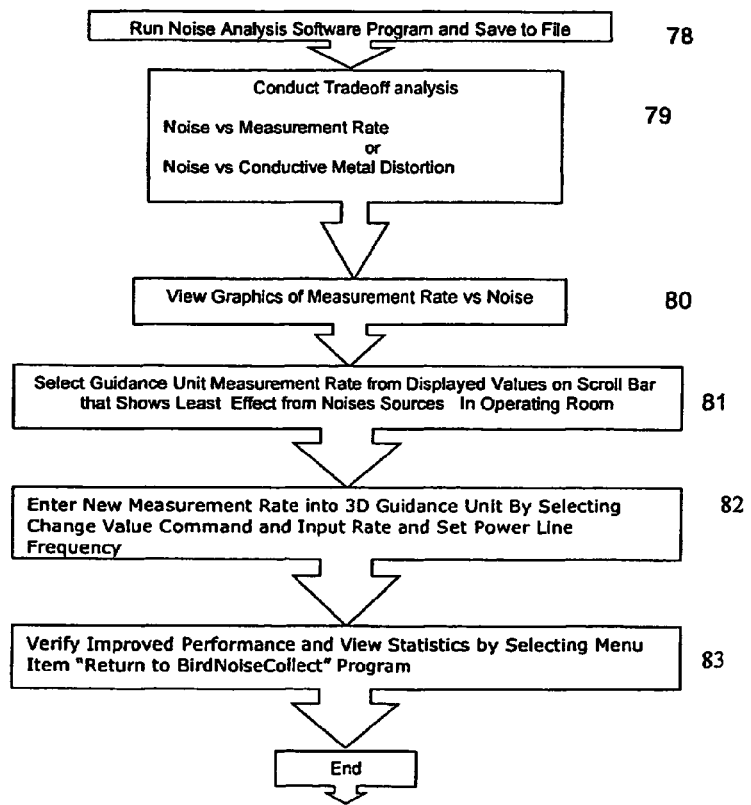

FIGS. 7*a*, 7*b* and 7*c* combine to show a flow chart showing implementation of noise reduction software for the DC magnetic guidance device as applied to a medical procedure. With reference to metal distortion's notoriety in undermining reliable use of an internal guidance device, noise in sensor measurements can be equally problematic. Because the DC sensor measures the magnetic fields emitted by the transmitter, it will also measure, any stray electromagnetic fields present in an operating room. These stray magnetic fields can cause the 3D guidance unit's position and orientation measurements to change slightly over time, even if the sensor is stationary. Hospital equipment that can cause noisy or "jittery" measurements includes: the power lines in the room, motors, pumps, elevators, computer displays and power transformers. If the interfering noise sources do not change their frequency of operation, then the interfering frequencies can be measured by a proprietary software program, developed by Ascension Technology Corporation, and the 3D guidance devices measurement rate adjusted to minimize the effects of this noise.

As shown in FIGS. 7*a*-*c*, the 3D Guidance Unit 70 is initially set-up to operate in a stand-alone mode, so that noise collection and analysis software programs 71 can be run to optimize the guidance unit's accuracy measurements by minimizing noise interference. The first step in the process is to position one miniaturized sensor on a non-metallic surface 72 in the field in which the procedure will be performed. The physician need not be present at this time, but a technician or nurse must power-up all medical equipment, normally used in the procedure. Directions are provided graphically in a series of graphical screens on the 3D guidance unit's display. These screens display error messages and troubleshooting instructions. It is important that the sensor not move during the data system configuration and collection period 73. Once this is accomplished, noise data is collected 84 and saved to system memory 75 as well as linked to the noise analysis software module that will be run next. Again, following on-screen instructions, the technician will set-up parameters to run the noise analysis module 76. To account for the power line frequency in the geographical location of the procedural room, the system will request entry of the power line frequency, 50 Hz or 60 Hz 77. This can also occur automatically by monitoring the incoming power line frequency. Now, the noise analysis module 78 can be run and data saved to file. In some procedures, measurement speed alone is the critical tracking requirement; in others, it may be conductive metal immunity. On-screen graphs and directions provide the technician with instruction to conduct a brief trade-off analysis 79 and view results graphically 80. For example, if measurement rate is most important, the technician will choose the fastest measurement rate that indicates the lowest noise rate. If immunity to nearby conductive metals is most important, then he will choose a lower measurement rate that enables the system to drive conductive errors to zero. Based on procedural requirements and knowledge of the 3D guidance system, the technician will select the measurement rate on a scroll bar that shows the least effect from noise sources in the given procedural room 81. This rate will be then be entered into the system 82. The performance improvement will be verified before the program is terminated and the unit ready for start of the medical procedure 83. Total time from start to end of this protocol is approximately 4 minutes.

Figure 8A:
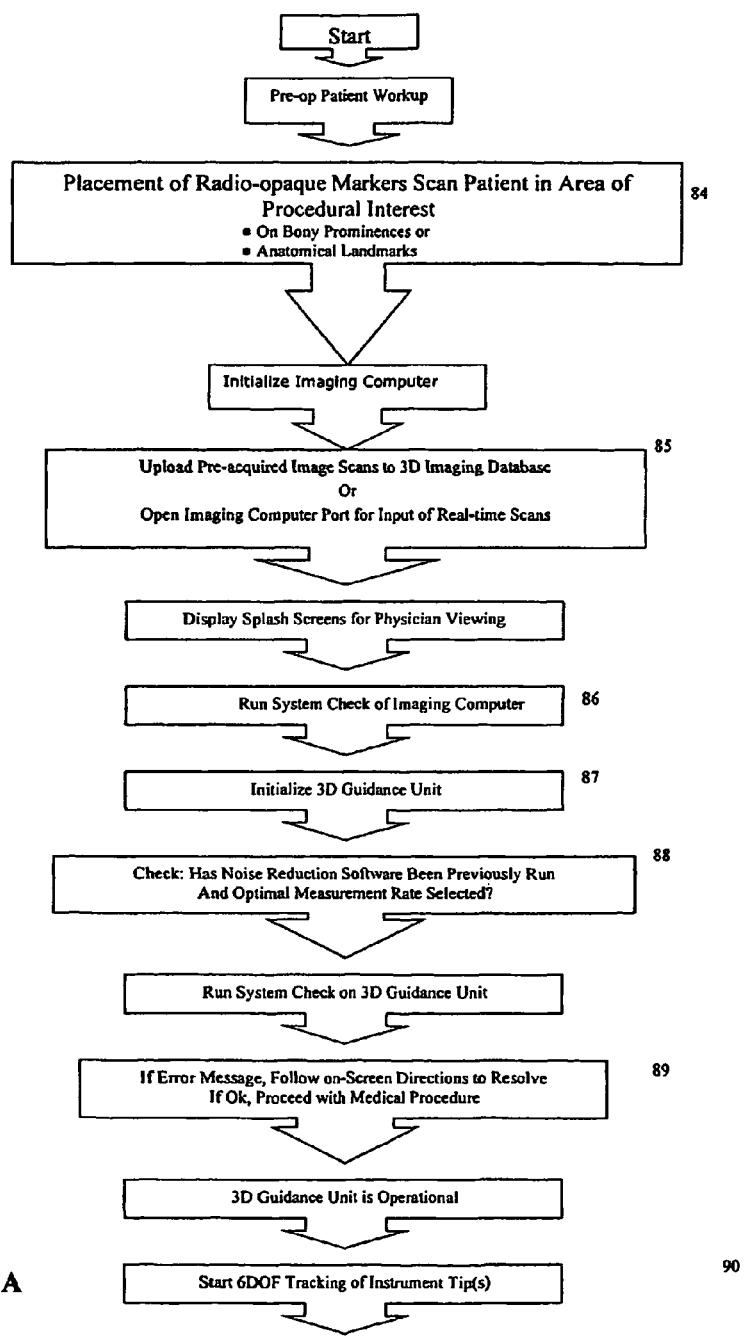
FIGS. 8a, 8b and 8c combine to show a flow chart of the steps required to implement 3D guidance in an image guided medical procedure.
Figure 8B:
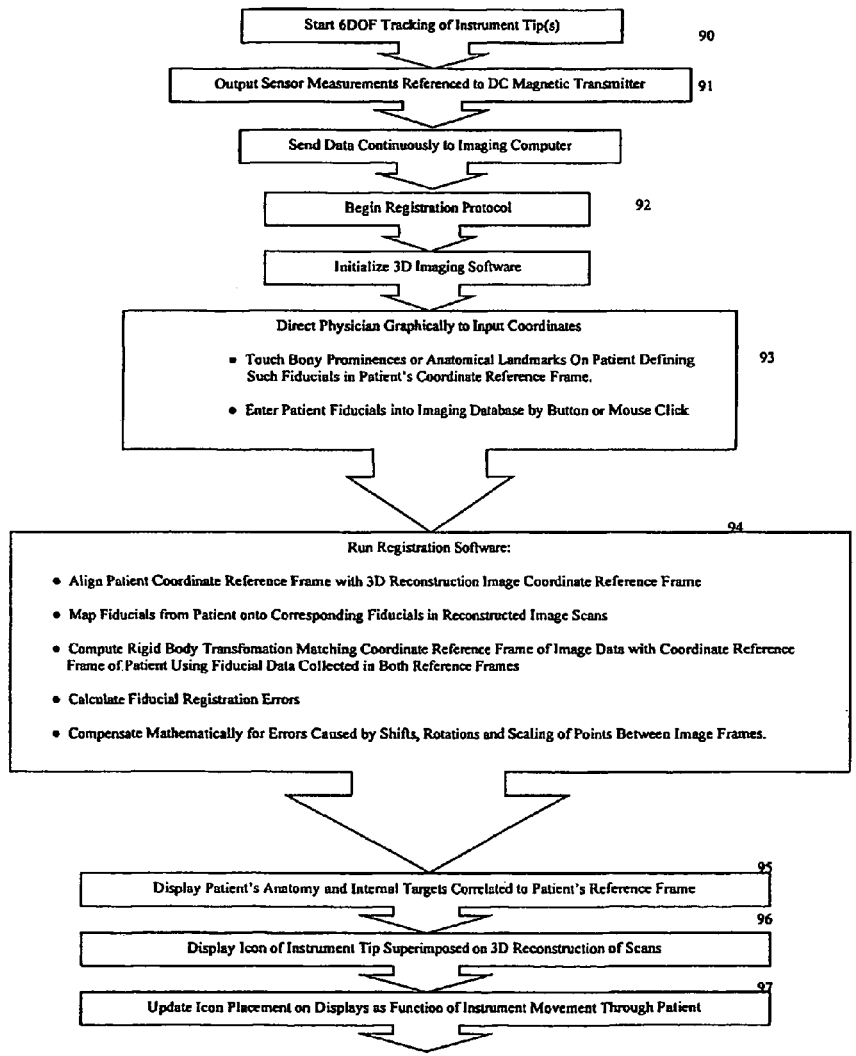
Figure 8C:
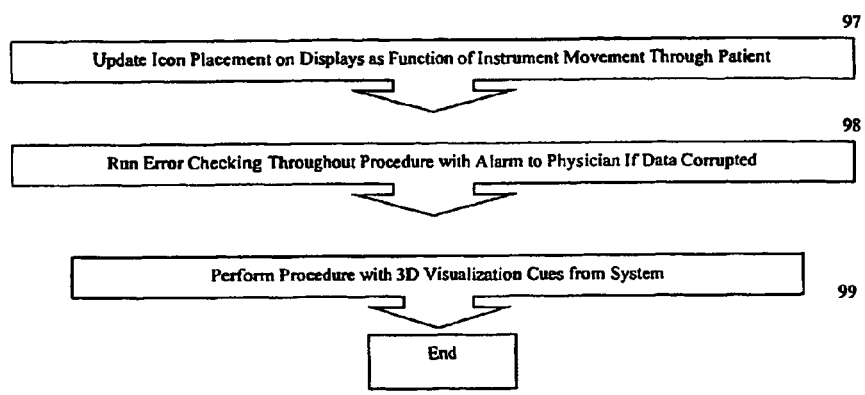

FIGS. 8*a*, 8*b* and 8*c* combine to show a flow chart of an image-guided medical procedure utilizing pulsed DC 6DOF tracking of a medical instrument. Typically, a pre-op patient work up will take place that includes placement of radio-opaque markers ("fiducials") on the patient prior to MRI, PET, and/or CAT scanning of the anatomical target area (84). Once the procedure starts, the imaging computer is initialized. The process includes uploading of digitally formatted pre-acquired scans to the imaging computer's database or, alternatively, starting a real-time imaging modality, such as an ultrasound or fluoroscope (85), that streams real-time digital images to the imaging computer. For safety reasons, the first of multiple system checks (86) is first performed, after which the physician sees a display screen of electronic medical images in at least three perspectives, along with the fiducials appearing as opaque markers on the anatomical images. Once this is accomplished, the 3D guidance unit is initialized (87) and a screen displays status of the noise check run before the start of the procedure (88), followed by a second system check indicating GO or NO GO status (89). If all systems are ready, tracking of the miniaturized sensor, embedded in the medical instrument, can START (90) with position and orientation measurements referenced to set 0, 0, 0, coordinate points on the transmitter (91). Now, the registration protocol can be initiated (92). A computer screen directs the physician to touch a number of reference points on patient corresponding to their previously "marked" locations on the image scans (93). Once these points are entered, by any number of means, into the imaging computer, a registration software program runs an algorithm (94) that aligns and maps the patient coordinate reference with the 3D reconstructed image coordinate reference frame. It further computes rigid body transformations so the frames can be matched, and also calculates fiducial registration errors. These errors are then input to a second algorithm designed to compensate mathematically for offsets caused by shifts, rotations, and scaling errors. Once accomplished, the system has automatically correlated the patient's electronic images with the movement of the surgical instrument—both of which are continuously displayed. At his time, trajectory of the instrument to the intended target can also be seen, correlated to the patient's reference frame (95). A 3D cursor or other virtual icon (96) indicative of the medical instrument's location in three-dimensional patient space is now interactively controllable by following visual cues on the imaging display screen (97).

At periodic intervals, a system check is run (98) to ensure that the instrument tip and its virtual icon continue to mirror one another's movement. The procedure can now be performed using 3D visualization cues to direct the physician to his 3D target within the 3D anatomy of the patient (99).

FIG. 9 is a flow chart of an image-guided medical procedure utilizing pulsed DC five or six degrees-of-freedom tracking of a medical instrument. Reference numeral 100 depicts the appropriate tracked surgical tool being selected by the surgeon. Typically, the sensor employed in the tool has already been optimized for size, range of tracking, signal-to-noise ratio, disposability, etc. This sensor is known to the tracker electronics via a memory device associated with the sensor. In a similar manner, the appropriate transmitter is selected in block 101. In this instance, however, the appropriate transmitter is determined by the environment, the procedure, and the surgeon's approach to the procedure. For example, an ENT procedure might require a compact transmitter, with a small tracking volume, to be mounted on the head. On the other hand, a cardiac ultrasound performed on a metal stretcher would be more adequately served by a flat, metal immune transmitter.

Once the sensor and transmitter are selected and the tracker electronics turned on, the surgeon can optimize the tracker's performance. In block 102, the surgeon selects a tracking system update rate for evaluation. The update rate can vary between high and low limits, depending on the system design. The update rate (for a dipole system) is determined by the time it takes to excite the three transmitter antennas. This sequence of excitations comprises: (1) The X coil of the transmitter is energized. It ramps up to a maximum and reaches a steady state. This steady state is maintained while eddy currents in surrounding metals decay and the sensor output values stabilize. The X coil is then turned off and an equal period is allowed to elapse. During this entire time, the sensor values are measured and summed; (2) Item (1) is repeated for the Y and Z coil. Because the update rate affects the frequency response of the system, varying the update rate can change the system's response to both random and non-random noise.

Once an update rate is chosen, the system collects data from the sensor with the transmitter off and determines its noise content. This occurs in block 103. Noise content can be determined by many ways known in the art, including using a Fast Fourier Transform and summing the power in the discrete frequency bins. The bin with the largest amplitude, hence the most noise, can also be determined and displayed to the surgeon. The step identified in block 104 is provided to help evaluate the results from block 103. This can be in the form of a comparison with previously calculated results from block 103 (searching for minimum noise power vs. update rate), being below a threshold value of power within one or some of the bins, etc. The step of block 104 may also include the use of a table of acceptable minimum and/or maximum update rates (or even rates to avoid for procedural or operational reasons) for different procedures. These values might be chosen to help avoid known environmental problems like low permeability metals or to help synchronize the tracker to a video signal. It would then limit its evaluation to update rates within the acceptable range. Blocks 102, 103 and 104 can also be performed by the tracker in an automated fashion.

Once the optimal update rate is chosen, the tracker filters can be optimized. The AC line notch filter requires a simple selection of the line frequency in use (50 or 60 Hz). This filter is used to remove noise caused by power mains. Its bandwidth can be changed between wide and narrow, with an associated change in latency and effectiveness. The wide setting applies a 6-tap notch finite impulse response (FIR) filter between 30 and 70 hertz. The narrow notch filter setting applies a 2-tap FIR filter. FIR filtering is well established in the art (see "Theory and Application of Digital Signal Processing," L. Rabiner and B. Gold, Prentice-Hall, Inc. 1975). The adaptive filter is an adaptive, infinite impulse response (IIR) low pass filter applied to the sensor data to eliminate high frequency noise. It is a two state weighted average between the current record and the previous frame. Variables are available for the weighting in the two filter states as well as the threshold values that tell the algorithm to switch states. The static state is utilized when the sensor is not moving. It has a small bandwidth. The dynamic state is used when the sensor is moving and has a larger bandwidth. Each variable can be treated as a table with values corresponding to different distances from the transmitter. A minimum value defines the static state filter's minimum allowable bandwidth, while a maximum value defines the dynamic filter's bandwidth. A threshold value defines when to switch between static and dynamic filters. Adaptive filters of this variety are well known in the art (see "Synthesis of an Optimal Set of Radar Track-While-Scan Smoothing Equations," T. Benedict and G. Bordner, IRE Transactions on Automatic Control, pp 27-32, July, 1962, pp 27-32. Also see "Fastrak Users Manual," OPM3609-002B, Polhemus, Inc., Colchester, Vt., USA, November 1992).

Block 105 indicates the selection and modification of all of the parameters associated with these filters. Once a set of values is selected, the system collects data from the sensor with the transmitter off and determines its noise content. This occurs in block 106. Noise content can be determined by many ways known in the art, including using a Fast Fourier Transform and summing the power in the discrete frequency bins. The bin with the largest amplitude, hence the most noise, can also be determined and displayed to the surgeon. The step in block 107 is provided to help evaluate the results from block 106. This can be in the form of a comparison with previously calculated results from block 106 (searching for minimum noise power vs. update rate), being below a threshold value of power within one or some of the bins, etc. The procedure described in block 107 could also include acceptable parameter ranges for different procedures. These values might be chosen to help avoid known environmental noise problems or allow for a certain dynamic response required by the procedure. It would then limit its evaluation to parameters within the acceptable range. The steps in blocks 105, 106 and 107 can also be performed by the tracker in an automated fashion.

Once the system is optimized to the environment, registration of the pre-operative image data to the tracker reference frame is performed. This occurs in block 108 using the methods noted previously. Once registered, the surgical procedure is performed in block 109.

As such, an invention has been disclosed in terms of preferred embodiments thereof which fulfill each and every one of the objects of the invention as set forth hereinabove, and provide a new and useful DC-based position and orientation monitoring system for tracking medical instruments of great novelty and utility.

Of course, various changes, alterations and modifications in the teachings of the present invention may be contemplated by those skilled in the art without departing from the intended spirit and scope thereof.

As such, it is intended that the present invention only be limited by the terms of the appended claims.

The invention claimed is:

1. Apparatus for determining the position and orientation of one or more points on a medical instrument relative to a reference frame in at least five degrees of freedom, comprising:
   a) a pulsed DC magnetic field transmitter, including at least one DC magnetic field generating element;
   b) a signal generation module, connected to said at least one generating element, said signal generation module comprising a digital to analog converter and a signal processor connected thereto, said digital to analog converter converting a digital signal to an analog signal and providing said analog signal to said at least one generating element of said pulsed DC magnetic field transmitter;
   c) a medical instrument including at least one pulsed DC magnetic field sensor, the sensor configured to be attached to said medical instrument by mounting the sensor on or in said medical instrument, said medical instrument configured to be located within a patient and said sensor not visible outside said patient during an operation phase, and configured to be located outside of the patient during a set-up phase;
   d) a 3D guidance electronics unit connected to said sensor;
   e) wherein said signal generation module is configured to produce one or more pulsed DC transmit signals whose pulse time is adjusted for optimal performance and is configured to provide said one or more transmit signals to said at least one generating element of said pulsed DC magnetic field transmitter, said 3D guidance electronics unit is configured to receive one or more detected signals from said sensor, wherein at least a portion of said one or more detected signals: (1) corresponds to said one or more pulsed DC transmitted signals, (2) is used to determine position and orientation of said sensor in at least five degrees of freedom from strength of said one or more pulsed DC transmitted signals and at least a portion of said one or more detected signals, and (3) indicates the position and orientation of one or more points on said medical instrument;
   f) a noise analysis module, wherein said noise analysis module is configured to determine noise data based on one or more detected signals from the sensor during the set-up phase, and to provide guidance to a user regarding selecting a pulse time for optimal performance based on the determination, wherein guidance comprises a comparison between one or more pulse times available for selection and the noise data;
   g) an imaging modality, connected to an imaging computer, said imaging modality capturing a plurality of 2D or 3D images of an anatomical region of interest of the patient; and said at least one pulsed DC magnetic field sensor connected to said imaging computer;
   h) wherein said imaging computer in communication with said 3D guidance electronics unit is configured to perform an operation to register the plurality of 2D or 3D images of the patient's anatomical region of interest with the said instrument within a patient; said imaging computer is configured to perform further operation to superimpose a cursor or icon representing said instrument onto the plurality of 2D or 3D images of the patient's anatomical region of interest; said cursor or icon is configured to move on, the plurality of 2D or 3D images of the patient's anatomical region of interest as a function of movement of said instrument being within the patient; and
   i) an imaging computer display configured to display the plurality of 2D or 3D images of the patient's anatomical region of interest with the superimposed cursor or icon of the medical instrument in a way such that a physician can intuitively orient said instrument within the patient to the image seen on any number of computer displays.

2. The apparatus of claim 1, wherein the pulse time that is selected for optimal performance comprises a pulse time that is selected to minimize effects of noise.

3. The apparatus of claim 1, wherein the 3D guidance electronic unit is configured to enable a technician to choose a fastest measurement rate that indicates a lowest noise rate.

4. The apparatus of claim 1, wherein the 3D guidance electronic unit is configured to enable a technician to choose a measurement rate that drives conductive errors to zero.

5. The apparatus of claim 1, wherein the 3D guidance electronic unit is configured to display a scroll bar that represents the pulse time.

6. The apparatus of claim 1, wherein the signal generation module is operated in accordance with a predetermined sequence.

7. The apparatus of claim 1, wherein the noise analysis module is configured to provide information relating to selecting a pulse time for optimal performance based on a power line frequency.

8. A medical device comprising:
   a) pulsed DC magnetic field sensor for detecting a plurality of pulsed DC magnetic fields, said pulsed DC magnetic field sensor is configured to be located within a patient and not visible outside said patient during an operation phase, and configured to be located outside of the patient during a set-up phase;
   b) a medical instrument to which said pulsed DC magnetic field sensor is attached;
   c) a 3D guidance electronics unit connected to said pulsed DC magnetic field sensor, and a pulsed DC magnetic field transmitter connected to said 3D guidance electronics unit, the pulsed DC magnetic field transmitter configured to produce one or more pulsed DC transmit signals whose pulse time is adjusted for optimal performance, whereby said electronics unit provides signals to said pulsed DC magnetic field transmitter and wherein said transmitter transmits said signals to said pulsed DC magnetic field sensor;
   d) an imaging computer with appropriate imaging software and memory and a display device, said imaging computer receiving signals resulting from pulsing of said magnetic fields;
   e) wherein said 3D guidance electronics unit is configured to receive pulsed DC magnetic field sensing information from said pulsed DC magnetic field sensor;
   f) wherein said 3D guidance electronics unit is configured to operate signal processing circuitry and software in association with said pulsed DC magnetic field sensing information to continuously track position and orientation of said pulsed DC magnetic field sensor within said patient in at least five degrees of freedom at one or more points on or within said medical instrument whose position and orientation is thus continuously tracked within said patient;

g) a noise analysis module, wherein said noise analysis module is configured to determine noise data based on one or more detected signals from the sensor during the set-up phase, and to provide guidance to a user regarding selecting a pulse time for optimal performance based on the determination, wherein guidance comprises a comparison between one or more pulse times available for selection and the noise data;

h) an imaging modality, connected to the imaging computer, said imaging modality capturing a plurality of 2D or 3D images of an anatomical region of interest of the patient; and said at, least one pulsed DC magnetic field sensor connected to the imaging computer;

i) wherein said imaging computer in communication with said 3D guidance electronics unit is configured to perform an operation to register the plurality of 2D or 3D images of the patient's anatomical region of interest with the said instrument within a patient; said imaging computer is configured to perform further operation to superimpose a cursor or icon representing said instrument onto the plurality of 2D or 3D images of the patient's anatomical region of interest; said cursor or icon is configured to move on said plurality of 2D or 3D images as a function of movement of said instrument being within the patient; and j) the display device is configured to display the plurality of 2D or 3D images of the patient's anatomical region of interest with the superimposed cursor or icon of the medical instrument in a way such that a physician can intuitively orient said instrument within the patient to the image seen on any number of computer displays.

9. The medical device of claim 8, wherein the pulse time that is selected for optimal performance comprises a pulse time that is selected to minimize effects of noise.

10. The medical device of claim 8, wherein the 3D guidance electronic unit is configured to enable a technician to choose a fastest measurement rate that indicates a lowest noise rate.

11. The medical device of claim 8, wherein the 3D guidance electronic unit is configured to enable a technician to choose a measurement rate that drives conductive errors to zero.

12. The medical device of claim 8, wherein the 3D guidance electronic unit is configured to display a scroll bar that represents the pulse time.

13. The apparatus of claim 8, wherein the noise analysis module is configured to provide information relating to selecting a pulse time for optimal performance based on a power line frequency.

14. Apparatus for determining the position and orientation of one or more points on a medical instrument relative to a reference frame in at least five degrees of freedom, comprising:

a) a pulsed DC magnetic field transmitter, including at least one DC magnetic field generating element;

b) a signal generation module, connected to said at least one generating element, said signal generation module comprising a digital to analog converter and a signal processor connected thereto, said digital to analog converter converting a digital signal to an analog signal and providing said analog signal to said at least one generating element of said pulsed DC magnetic field transmitter;

c) a medical instrument including at least one pulsed DC magnetic field sensor, the sensor configured to be attached to said medical instrument by mounting the sensor on or in said medical instrument, said medical instrument configured to be located within a patient and said sensor not visible outside said patient during an operation phase, and configured to be located outside of the patient during a set-up phase;

d) a 3D guidance electronics unit connected to said sensor;

e) wherein said signal generation module is configured to produce one or more pulsed DC transmit signals whose pulse time is adjusted for optimal performance and is configured to provide said one or more transmit signals to said at least one generating element of said pulsed DC magnetic field transmitter, said 3D guidance electronics unit is configured to receive one or more detected signals from said sensor, wherein at least a portion of said one or more detected signals: (1) corresponds to said one or more pulsed DC transmitted signals, (2) is used to determine position and orientation of said sensor in at least five degrees of freedom from strength of said one or more pulsed DC transmitted signals and at least a portion of said one or more detected signals, and (3) indicates the position and orientation of one or more points on said medical instrument;

f) a noise analysis module, wherein said noise analysis module is configured to determine noise data based on one or more detected signals from the sensor during the set-up phase, and to provide guidance to a user regarding selecting a pulse time for optimal performance based on the determination, wherein guidance comprises a comparison between one or more pulse times available for selection and the noise data;

g) an ultrasound detector, connected to an imaging computer, said ultrasound detector capturing a plurality of 2D or 3D ultrasound frames of an anatomical region of interest of the patient; and said at least one pulsed DC magnetic field sensor connected to said imaging computer;

h) a position and orientation sensor that detects pulsed DC magnetic fields, mounted in or on the ultrasound detector to determine its 3D location, said position and orientation sensor detecting position and orientation of each of said plurality of 2D or 3D ultrasound frames of the patient's anatomical region of interest;

i) wherein said imaging computer in communication with said 3D guidance electronics unit is configured to perform an operation to register said plurality of 2D or 3D ultrasound frames of the patient's anatomical region of; interest with the said instrument within a patient; said imaging computer is configured to perform further operation to superimpose a cursor or icon representing said instrument onto said plurality of 2D or 3D ultrasound frames of the patient's anatomical region of interest; said cursor or icon is configured to move on said plurality of 2D or 3D ultrasound frames of the patient's anatomical region of interest as a function of movement of said instrument being within the patient; and is configured to construct an image from said plurality of 2D or 3D ultrasound frames of the patient's anatomical region of interest and the detected position and orientation of each of said frames with respect to the detected position and orientation of one or more points on said medical instrument; and j) an imaging computer display configured to display the plurality of 2D or 3D ultrasound frames of the patient's anatomical region of interest with the superimposed cursor or icon of the medical instrument in a way such that a physician can intuitively orient said instrument within the patient to the image seen on any number of computer displays.

15. The apparatus of claim 14, wherein the signal generation module is operated in accordance with a predetermined sequence.

16. The apparatus of claim 14, wherein the pulse time that is selected for optimal performance comprises a pulse time that is selected to minimize effects of noise.

17. The apparatus of claim 14, wherein the 3D guidance electronic unit is configured to enable a technician to choose a fastest measurement rate that indicates a lowest noise rate.

18. The apparatus of claim 14, wherein the 3D guidance electronic unit is configured to enable a technician to choose a measurement rate that drives conductive errors to zero.

19. The apparatus of claim 14, wherein the 3D guidance electronic unit is configured to display a scroll bar that represents the pulse time.

20. The apparatus of claim 14, wherein the noise analysis module is configured to provide information relating to selecting a pulse time for optimal performance based on a power line frequency.

\* \* \* \* \*

UNITED STATES PATENT AND TRADEMARK OFFICE
CERTIFICATE OF CORRECTION

PATENT NO.       : 8,942,780 B2
APPLICATION NO.  : 12/924476
DATED            : January 27, 2015
INVENTOR(S)      : Jack Thomas Scully and Mark Robert Schneider Page 1 of 1

It is certified that error appears in the above-identified patent and that said Letters Patent is hereby corrected as shown below:

In the Claims

Column 23, Line 16, In Claim 8, delete "at, least" and insert -- at least --

Column 24, Line 49, In Claim 14, delete "of;" and insert -- of --

Signed and Sealed this
Twenty-eighth Day of April, 2015

Michelle K. Lee
*Director of the United States Patent and Trademark Office*